US011459313B2

(12) United States Patent
Emadi et al.

(10) Patent No.: US 11,459,313 B2
(45) Date of Patent: Oct. 4, 2022

(54) AZIRIDINYL AND AMINO DIMERIC NAPHTHOQUINONE COMPOUNDS AND USE FOR ACUTE MYELOID LEUKEMIA

(71) Applicants: University of Maryland, Baltimore, Baltimore, MD (US); MCDANIEL COLLEGE, Westminster, MD (US)

(72) Inventors: Ashkan Emadi, Clarksville, MD (US); Rena G. Lapidus, Baltimore, MD (US); Brandon A. Carter-Cooper, Manchester, MD (US); Steven Fletcher, Baltimore, MD (US); Dana Ferraris, Eldersburg, MD (US); Edward A. Sausville, Edgewater, MD (US)

(73) Assignees: UNIVERSITY OF MARYLAND, BALTIMORE, Baltimore, MD (US); MCDANIEL COLLEGE, Westminster, MD (US)

( * ) Notice: Subject to any disclaimer, the term of this patent is extended or adjusted under 35 U.S.C. 154(b) by 290 days.

(21) Appl. No.: 16/344,733

(22) PCT Filed: Oct. 5, 2017

(86) PCT No.: PCT/US2017/055380
§ 371 (c)(1),
(2) Date: Apr. 24, 2019

(87) PCT Pub. No.: WO2018/067842
PCT Pub. Date: Apr. 12, 2018

(65) Prior Publication Data
US 2020/0283417 A1 Sep. 10, 2020

Related U.S. Application Data

(60) Provisional application No. 62/546,644, filed on Aug. 17, 2017, provisional application No. 62/404,262, filed on Oct. 5, 2016.

(51) Int. Cl.
*C07D 403/10* (2006.01)
*A61P 35/02* (2006.01)
*C07C 225/30* (2006.01)
*C07D 203/14* (2006.01)
*A61K 45/06* (2006.01)

(52) U.S. Cl.
CPC ............ *C07D 403/10* (2013.01); *A61P 35/02* (2018.01); *C07C 225/30* (2013.01); *C07D 203/14* (2013.01); *A61K 45/06* (2013.01)

(58) Field of Classification Search
None
See application file for complete search history.

(56) References Cited

U.S. PATENT DOCUMENTS

| 4,806,531 A | 2/1989 | Sartorelli et al. |
| 2013/0150437 A1 | 6/2013 | Jiang et al. |

FOREIGN PATENT DOCUMENTS

| WO | 2015050844 A1 | 4/2015 |
| WO | 2018067842 A1 | 4/2018 |

OTHER PUBLICATIONS

Forrester, et al., Journal of the Chemical Society, Perkin Transactions 1, 12:1115. (Year: 1975).*
Forrester et al., Persulfate Oxidations. XL Oxidative Dimerization of Aminonaphthoquinones, Journal of the Chemical Society, Perkin Transactions 1: Organic and Bio-Organic Chemistry, 1975, pp. 1115-1120, vol. 12.
Laatsch, Synthese hydroxylierter Binaphthochinone duich Amin/ Hydroxyl-Austausch—Uber die Umsetzung von 2,2'-Binaphthy1-1,4;1 1,4'-dichinonen mit Piperidin / Synthesis of Hydroxylated Binaphthoquinones via Amine/Hydroxyl Exchange—On the Reaction of 2,2'-Binaphthy1-1,4;1 1,4'-diquinones with Piperidine, Journal of Chemical Sciences, 1989, pp. 1271-1278, vol. 44.
European Search Report, in European Application No. 17859198.8, dated Mar. 23, 2020, pp. 1-7.
Lapidus et al., Hydroxylated Dimeric Naphthoquinones Increase the Generation of Reactive Oxygen Species, Induce Apoptosis of Acute Myeloid Leukemia Cells and Are Not Substrates of the Multidrug Resistance Proteins ABCB1 and ABCG2, Pharmaceuticals, 2016, pp. 1-15, vol. 9.
Allibbai, S., et al., "Outcomes and quality of care in acute myeloid leukemia over 40 years", "Cancer", Jul. 1, 2009, pp. 2903-2911, vol. 115, No. 13, Publisher: 2009 American Cancer Society, Published in: DOI: 10.1002/cncr.24373.
Carter-Cooper, B., et al., "Synthesis, characterization and antineoplastic activity of bis-aziridinyl dimeric naphthoquinone A novel class of compounds with potent activity against acute myeloid leukemia cells", "Bioorganic & Medicinal Chemistry Letters", Jan. 1, 2017, pp. 6-10, vol. 27, No. 1, Publisher: Elsevier, Published in: https://doi.org/1 0.1016/j.bmcl.2016.11.045.
Chakrabarti, G., et al., "Targeting glutamine metabolism sensitizes pancreatic cancer to PARP-driven metabolic catastrophe induced by -lapachone", "Cancer & Metabolism", Oct. 12, 2015, pp. 1-12, vol. 3, No. 12, Publisher: BioMed Central, Published in: DOI 10.1186/ s40170-015-0137-1.
Danson, S., et al., "Phase I pharmacokinetic and pharmacodynamic study of the bioreductive drug RH1", "Annals of Oncology: European Society for Medical Oncology", Mar. 4, 2011, pp. 1653-1660, vol. 22, No. 7, Publisher: Oxford University Press, Published in: https://doi.org/10.1093/annonc/mdq638.
Eberlein, U., et al., "Calibration of the -H2AX DNA Double Strand Break Focus Assay for Internal Radiation Exposure of Blood Lymphocytes", "PLOS One", Apr. 8, 2015, pp. 1-11, Published in: DOI:10.1371/journal.pone.0123174.

(Continued)

Primary Examiner — Michael Barker
(74) Attorney, Agent, or Firm — Wolter Van Dyke Davis, PLLC; Eugene J. Molinelli; Martha Cassidy

(57) ABSTRACT

The invention relates to new amino dimeric naphthoquinone compounds with antileukemic activity. Compounds of the invention demonstrated increased aqueous solubility compared to previously available dimeric naphthoquinones and potent nanomolar inhibition of cell survival in AML cells. Preferred compounds contained an aziridine or a secondary amino alcohol pharmacophore.

22 Claims, 12 Drawing Sheets

(56) References Cited

OTHER PUBLICATIONS

Emadi, A., et al., "Cyclophosphamide and cancer: golden anniversary", "Clinical Oncology", Nov. 2009, pp. 638-647, vol. 6, Publisher: Nature Reviews, Published in: DOI: 10.1038/nrclinonc.2009. 146.
Emadi, A., et al., "Regiocontrolled Synthesis of the Trimeric Quinone Framework of Conocurvone", "Organic Letters", Jan. 22, 2002, pp. 521-524, vol. 4, No. 4, Publisher: American Chemical Society, Published in: DOI 10.1021/ol010272m.
Emadi, A., et al., "A Chemical Genetic Screen for Modulators of Asymmetrical 2,2-Dimeric Naphthoquinones Cytotoxicity in Yeast", May 26, 2010, pp. 1-13, vol. 5, No. 5, Publisher: PLoS One, Published in: https://doi.org/10.1371/journal.pone.0010846.
Emadi, A., et al., "Metabolic and electrochemical mechanisms of dimeric naphthoquinones cytotoxicity in breast cancer cells", "Bioorganic and Medicinal Chemistry", Oct. 8, 2011, pp. 7057-7062, vol. 19, Publisher: Elsevier, Published in: doi: 10.1016/j.bmc. 2011.10.005.
Emadi, A., and Karp, J., "The clinically relevant pharmacogenomic changes in acute myelogenous leukemia", "Pharmacogenomics", Aug. 2012, pp. 1257-1269, vol. 13, No. 11, Published in: doi: 10.2217/pgs.12.102.
Emadi, A., and Karp, J., "The state of the union on treatment of acute myeloid leukemia", "Leukemia & Lymphoma", Mar. 25, 2014, pp. 2423-2425, vol. 55, No. 11, Published in: DOI: 10.3109/10428194.2014.897705.
Frank, N., et al., "Comparative effects of doxorubicin and a doxorubicin analog, 13-deoxy, 5-iminodoxorubicin (GPX-150), on human topoisomerase II activity and cardiac function in a chronic rabbit model", "Invest New Drugs", Aug. 31, 2016, pp. 693-700, vol. 34, Publisher: Springer Science+Business Media, Published in: DOI 10.1007/s10637-016-0388-x.
Hole, P., et al., "Do reactive oxygen species play a role in myeloid leukemias?", "Blood", Mar. 11, 2011, pp. 5816-5826, vol. 117, No. 22, Publisher: The American Society of Hematology, Published in: doi: https://doi.org/10.1182/blood-2011-01-326025.
ISA/US, "International Search Report and Written Opinion for International Patent Application No. US 17/55380 dated Dec. 28, 2017", pp. 1-7, Publisher: International Searching Authority US, Published in: Alexandria, VA.
Lapidus, R., et al., "Hydroxylated Dimeric Naphthoquinones Increase the Generation of Reactive Oxygen Species, Induce Apoptosis of Acute Myeloid Leukemia Cells and Are Not Substrates of the Multidrug Resistance Proteins ABCB1 and ABCG2", "Pharmaceuticals", Jan. 19, 2016, pp. 1-15, vol. 9, No. 4, Published in: doi: 10.3390/ph9010004.
Oran, B., et al., "Survival For Older Patients With Acute Myeloid Leukemia: A Population-Based Study", "Haematologica", Dec. 2012, pp. 1916-1924, vol. 97, No. 12, Published in: Doi:10.3324/haematol.2012.066100.
Papaemmanuil, E., et al., "Genomic Classification and Prognosis in Acute Myeloid Leukemia", "N Engl J Med", May 9, 2016, pp. 2209-2221, vol. 374, No. 23, Published in: DOI: 10.1056/NEJMoa1516192.
Patel, J., et al., "Prognostic Relevance of Integrated Genetic Profiling in Acute Myeloid Leukemia", "N Engl J Med", Mar. 22, 2012, pp. 1079-1089, vol. 366, No. 12, Published in: DOI: 10.1056/NEJMoa1112304.
Pidugu, L., et al., "A direct interaction between NQO1 and a chemotherapeutic dimeric naphthoquinone", "BMC Structural Biology", Jan. 28, 2016, pp. 1-10, vol. 16, No. 1, Published in: DOI 10.1186/s12900-016-0052-x.
PubChem, "PubChem CID: 376950, 2-(2-(Dimethlamino)ethylamino) naphthazarin deposited on Mar. 26, 2005 and modified on Nov. 4, 2017", "National Center for Biotechnology Information", pp. 1-13, Publisher: NIH US National Library of Medicine.
Pubchem, "PubChem CID: 4428739, CHEMBL396799; 3-(2-hydroxylamino)diospyrin diethylether deposited on Nov. 19, 2009 and modified on Nov. 4, 2017", "National Center for Biotechnology Information", pp. 1-11, Publisher: US National Library of Medicine.
Ross, A., et al., "Dimeric naphthoquinones, a novel class of compounds with prostate cancer cytotoxicity", "BJU International", Sep. 1, 2010, pp. 447-454, vol. 108, Published in: doi:10.1111/j.1464-410X.2010.09907.x.
Stafliano, K., et al., "Regioconliolled synthesis and HIV inhibitory activity of unsymmetrical binaphthoquinone and trimeric naphthoquinone derivatives of conocurvone", "Bioorganic & Medicinal Chemistry", Aug. 15, 2006, pp. 5651-5665, vol. 14, Publisher: Elsevier, Published in: https://doi.org/10.1016/j.bmc.2006.04.034.
Turinetto, V., et al., "H2AX phosphorylation level in peripheral blood mononuclear cells as an event-free survival predictor for bladder cancer", "Molecular Carcinogenesis", Nov. 19, 2015, pp. 1833-1842, vol. 55, No. 11, Publisher: Wiley, Published in: https://doi.org/10.1002/mc.22431.
Verma, R., "Anti-Cancer Activities of 1,4-Naphthoquinones: A QSAR Study", "Anti-Cancer Agents in Medicinal Chemistry", 2006, pp. 489-499, vol. 6, No. 5, Publisher: Bentham Science Publishers, Ltd., Published in: DOI: 10.2174/187152006778226512.
Wellington, K., "Understanding cancer and the anticancer activities of naphthoquinones—a review", "Royal Society Chemistry Advances", Feb. 5, 2015, pp. 20309-20338, vol. 5, Published in: DOI: 10.1039/C4RA13547D.
Workman, P., "Enzyme-directed bioreductive drug development revisited: a commentary on recent progress and future prospects with emphasis on quinone anticancer agents and quinone metabolizing enzymes, particularly DT-diaphorase", "Oncol. Res.", 1994, pp. 461-475, vol. 6, No. 10/11, Publisher: Elsevier Science Ltd, Published in: USA.
Xiang, M., et al., "Gene expression-based discovery of atovaquone as a STAT3 inhibitor and anticancer agent", "Blood Journal", Oct. 6, 2016, pp. 1845-1853, vol. 128, No. 14, Publisher: The American Society of Hematology, Published in: DOI 10.1182/blood-2015-07-660506.

\* cited by examiner

| Agent | IC50 MV411 (μM) | MOLM14 (μM) |
|---|---|---|
| Compound A | 0.16 ± 0.01 | 0.2 ± 0.04 |
| Mitomycin C | 0.12 ± 0.01 | 0.02 ± 0.001 |
| Atovaquone | >5 | >5 |
| Coenzyme Q10 | >25 | >25 |
| Daunorubicin | 0.03 ± 0.03 | 0.01 ± 0.01 |
| Vitamin K | >5 | >5 |

MOLM-14

THP-1

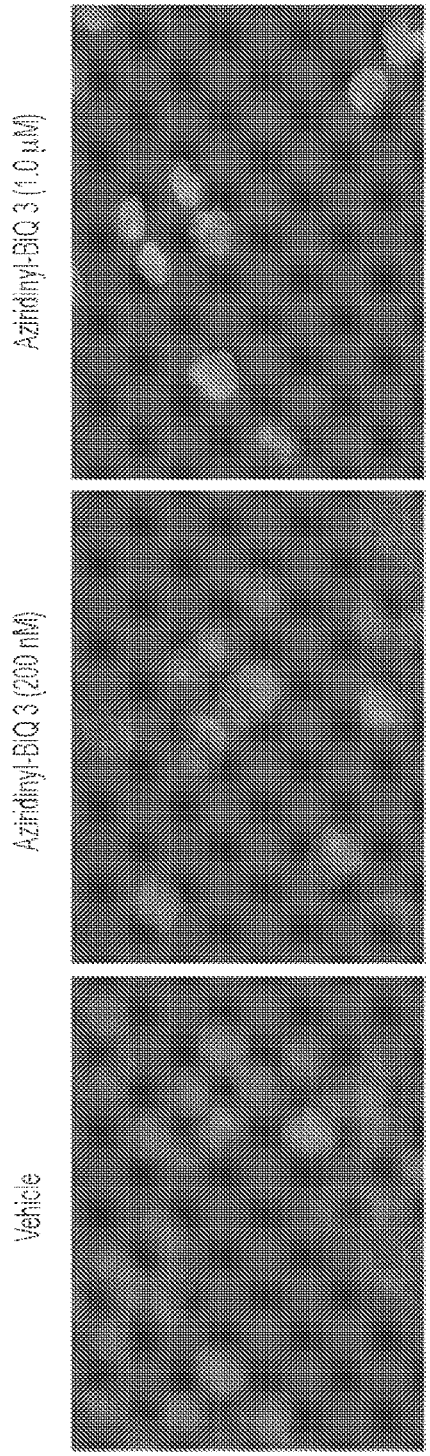
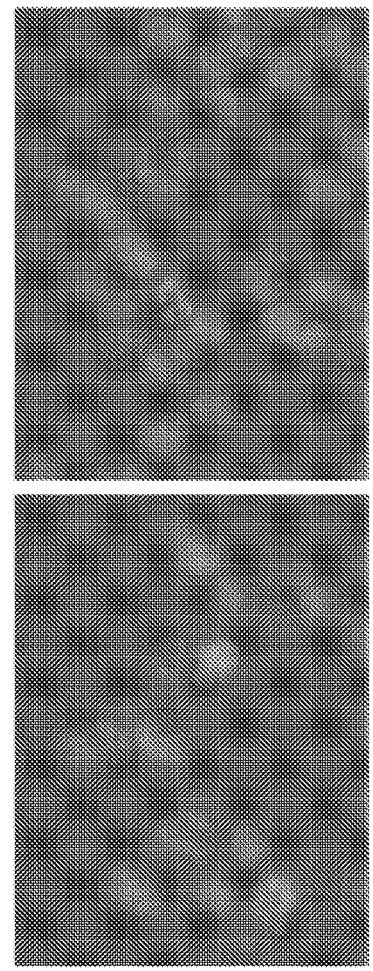
FIG. 7A Vehicle
FIG. 7B Aziridinyl-BIQ 3 (200 nM)
FIG. 7C Aziridinyl-BIQ 3 (1.0 µM)
FIG. 7D Aziridinyl-BIQ 3 (2.0 µM)
FIG. 7E Irradiated Control

AZIRIDINYL AND AMINO DIMERIC NAPHTHOQUINONE COMPOUNDS AND USE FOR ACUTE MYELOID LEUKEMIA

CROSS-REFERENCE TO PRIOR APPLICATIONS

This application claims benefit to prior applications U.S. provisional application Ser. No. 62/404,262, filed Oct. 5, 2016 and U.S. provisional application Ser. No. 62/546,644, filed Aug. 17, 2017. The contents of these applications are hereby incorporated by reference in their entirety.

STATEMENT OF FEDERALLY SPONSORED RESEARCH AND DEVELOPMENT

This invention was made with Government support under grant CA134274 awarded by the National Institutes of Health. The Government has certain rights in the invention.

BACKGROUND

1. Field of the Invention

The present invention generally relates to the field of medicine and in particular to the preferred bis-amino alcohol dimeric naphthoquinone compounds of the invention that exhibit anti-neoplastic activity against cancer cells, including acute myeloid leukemia (AML) cells.

2. Background of the Invention

Acute myeloid leukemia (AML; also known as acute myeloblastic leukemia, acute myelogenous leukemia, acute granulocytic leukemia or acute nonlymphocytic leukemia) is a cancer of the blood and bone marrow in which the bone marrow makes abnormal myeloblasts, red blood cells, or platelets. It usually is an aggressive cancer if not treated.

Treating AML is challenging because it is an extremely heterogeneous disease with various leukemogenic mutations and cytogenetic abnormalities with poorly understood interplay among them in each patient. The clinical outcomes of patients with acute myeloid leukemia (AML) treated with the available cytotoxic, targeted, and hematopoietic stem cell transplant therapy remains unsatisfactory with 3-8% survival at 5 years in patients aged 60 years and older and up to 50% in patients younger than 60 years of age.

The problem of inadequate treatment options for AML is exacerbated by an upsurge in the incidence of AML to approximately 20,000 new cases in 2014. Unfortunately, the mainstay of therapy for AML has not changed significantly for the last 40 years. The only drug approved of the treatment of AML in the last few decades has been gemtuzumab ozogamicin, which subsequently was withdrawn from the market when benefit was not seen in the confirmatory clinical trials.

Currently, chemotherapy is used to attempt remission of the disease. Compounds with quinone moieties are frequently used for treatment of solid and hematologic neoplasms. These compounds, such as mitomycin-C and RH1 (benzoquinone), daunorubicin, doxorubicin, idarubicin, epirubicin, aclarnbicin and mitoxantrone (anthraquinone), and atovaquone, 2,2'-binaphthoquinones and β-lapachone (naphthoquinone) are among the most investigated anticancer agents, preclinically and clinically. For AML, combination chemotherapy with cytarabine and an anthracycline is most commonly used.

The cytotoxic mechanisms of action of quinone compounds include (i) formation of semiquinone radicals and quinone redox cycling that results in initiation and propagation of intracellular free oxygen radical chain reactions, (ii) nicotinamide adenine dinucleotide phosphate (NADPH) depletion via interference with the enzyme NAD(P)H:quinone oxidoreductase 1(NQO1), (iii) nicotinamide adenine dinucleotide (NAD) depletion via hyperactivation of poly (ADP ribose) polymerase (PARP), and (iv) inhibition of DNA topoisomerase-II. Nevertheless, neoplastic cells tend to become resistant to these agents. In addition, stem cell transplants (bone marrow transplants) are used to replace unhealthy bone marrow with stem cells that can regenerate new, healthy bone marrow.

Thus, there is an urgent need for development of new therapeutic agents and strategies for AML treatment. In particular, there is a need in the art for quinone-based anticancer agents that can overcome drug resistance in malignant cells.

SUMMARY OF THE INVENTION

Therefore, the present invention relates to aziridinyl and other amino dimeric naphthoquinones designed and synthesized to have up to 10-fold more potency in cell proliferation assays (IC50=200-500 nM) compared to first generation non-aziridinyl containing dimeric naphthoquinones, on AML cell lines and primary AML cells from patients. Dimeric naphthoquinones kill AML cells by induction of oxidative stress and disrupting mitochondrial membrane potential. The aziridinyl containing dimeric naphthoquinones of the invention have triple modes of action in cancer cells, (1) inducing cellular oxidative stress, (2) damaging DNA, and (3) interacting with cellular proteins involves in oxidative response.

The invention relates to a compound according to Formula A,

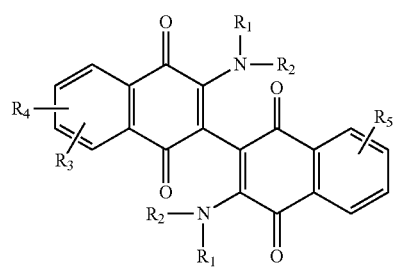

Formula A wherein $R_1$ and $R_2$, independently are the same or different and are selected from the group consisting of —Cl, —Br, —I, —F, —H, —CH$_3$, —CH$_2$CH$_3$, —CH$_2$OH, —CH$_2$CH$_2$OH, —CH(CH$_2$OH)$_2$, —CH=CHOH, —CH$_2$CH(CH$_3$)OH, —CH$_2$CH(CH$_3$)CH$_2$CH$_2$OH, —CH$_2$CH$_2$OCH$_2$ OH, —CH$_2$CH$_2$OCH$_2$CH$_2$OH, —CH$_2$CH$_2$OCH$_3$, —CH$_2$ CH$_2$OCOCH$_3$, —CH$_2$NH$_2$, —CH$_2$NHCH$_3$, —CH$_2$N (CH$_3$)$_2$, —CH$_2$CH$_2$N(CH$_3$)$_2$, and —CH$_2$X, or $R_1$ and $R_2$ can be joined to form a cyclic 1-piperizino or

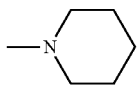

1-piperidino, which optionally is substituted at the 4-position with hydroxyl, hydroxymethyl, —CH$_2$CH$_2$OCH$_2$OH, or —CH$_2$CH$_2$OCH$_2$CH$_2$OH,

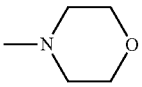

morpholino or aziridino; and wherein R$_3$ and R$_4$, independently are the same or different and are selected from the group consisting of —H, —NH$_2$, —X, —CH$_3$ optionally substituted with one or more X, —OH, OCH$_3$ optionally substituted with one or more X, —OCH$_2$CH$_3$ optionally substituted with one or more X, —OCH$_2$CH$_2$CH$_3$ optionally substituted with one or more X, —CH$_2$OCH$_3$ optionally substituted with one or more X, —C(O)CH$_3$, —C(O)H, —C(O)OH, —CH$_2$C(O)OH, —NO$_2$, —CH$_2$NO$_2$, —CN, and —CH$_2$CN, and —SO$_2$—R$_5$; wherein X is halo and R$_5$ is H or C$_{1-3}$alkyl;

or a salt, hydrate, or solvate thereof.

Preferred compounds are those wherein R$_1$ and R$_2$ independently are the same or different and include aziridino, hydroxyl, chloro, —CH$_2$CH$_2$OH and —CH$_2$CH$_2$N(CH$_3$)$_2$, and/or wherein R$_3$ and R$_4$ independently are the same or different and include —H, —F, —Cl, —CF$_3$, —OH, —OCH$_2$CH$_3$ and —OCH$_3$.

Most preferred compounds include

Compound 101

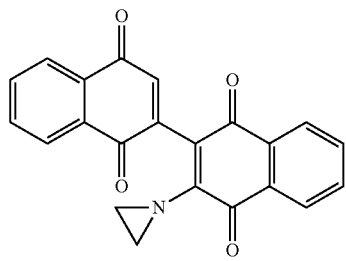

(3,3'-bis(aziridine)-2,2'-binaphthoquinone)

Compound 102

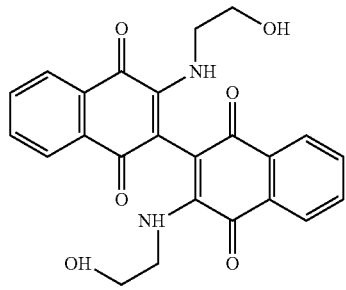

(3,3'-bis(2-aminoethanol)-2,2'-binaphthoquinone)

Compound 103

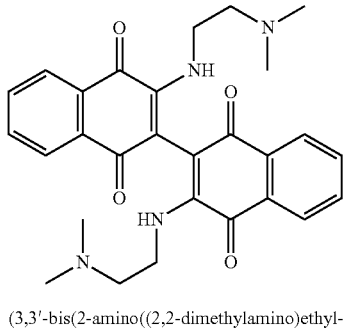

(3,3'-bis(2-amino((2,2-dimethylamino)ethyl-2,2'-binaphthoquinone)

Compound 104

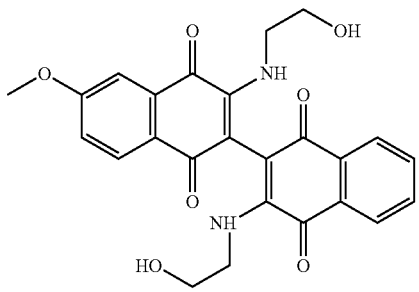

(6-methoxy, 3,3'-bis(2-aminoethanol)-2,2'-binaphthoquinone)

Compound 105

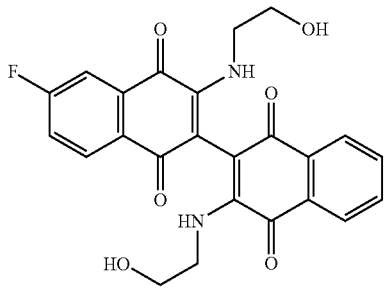

and (6-fluoro, 3,3'-bis(2-aminoethanol)-2,2'-binaphthoquinone)

Compound 106

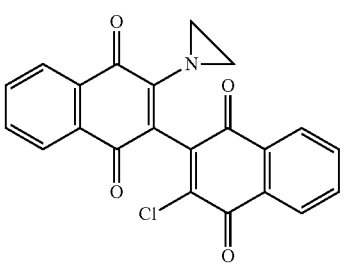

(3-(aziridin-1-yl)-3'-chloro-[2,2'-binaphthalene]-1,1' 4,4'-tetrone or any salt, hydrate, or solvate thereof.

The invention also includes pharmaceutical compositions comprising any of the compounds discussed above and a pharmaceutically acceptable carrier.

The invention also includes a method of treating leukemia comprising administering to a subject in need the pharmaceutical composition discussed herein. Preferably, the leukemia is acute myeloid leukemia.

The invention also relates to a method of treating acute myeloid leukemia comprising administering to a subject in need a pharmaceutical compositions discussed herein, optionally with a second agent, for example drugs used to treat AML, including Cytarabine, Daunorubicin, Daunomycin, Idarubicin, mitoxantrone, Cladribine, Fludarabine, Topotecan, Etoposide, 6-thioguanine, Hydroxyurea, Methotrexate, 6-mercaptopurine, Azacitidine, and Decitabine.

BRIEF DESCRIPTION OF THE DRAWINGS

FIG. 6A and THP-1, FIG. 6B) after treatment with Compound 101.

FIG. 7A, FIG. 7B, FIG. 7C, FIG. 7D, and FIG. 7E are photographs of MOLM-14 cells with γ-H2Ax phosphorylation showing DNA damage. FIG. 7A: vehicle; FIG. 7B: Compound 101 (200 nM); FIG. 7C: Compound 101 (1 μM); FIG. 7D: Compound 101 (2.0 μM); FIG. 7E: irradiated control.

DETAILED DESCRIPTION OF PREFERRED EMBODIMENTS

1. INTRODUCTION

Figure 1:
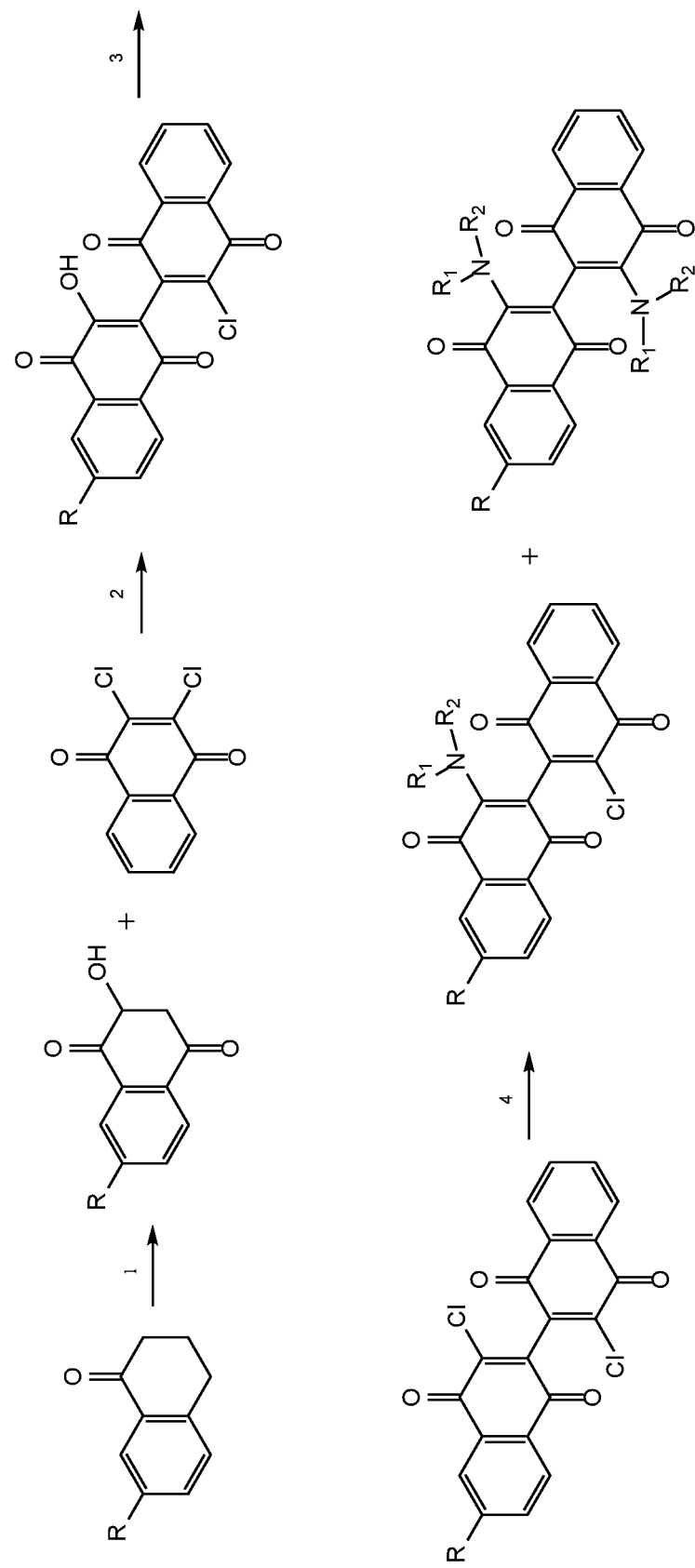
FIG. 1 shows a detailed chemical synthesis for production of dimeric naphthoquinone compounds, Scheme 3. Reaction 1: $Re_2(CO)10$, $O_2$, dioxane; reaction 2: $CaCO_3$ 85%; reaction 3: $SOCl_2$ 81%; reaction 4: $HNR_1R_2$ 3-80%.

An important characteristic of AML blasts is that they can escape host immune surveillance, mediated in part by overexpression of the tryptophan metabolizing enzyme, indoleamine 2,3-dioxygenase (IDO). Evidence indicates that AML cells are susceptible to compounds like anthracyclines and mitoxantrone that perturb the oxidative state of the cell. These drugs are members of a group of anti-neoplastic compounds known as naphthoquinones. The naphthoquinone moiety occurs in many natural products and is directly responsible for disrupting the oxidative state of the cell. One of the hallmarks of AML blasts is a disrupted cellular oxidative state resulted from elevated level of reactive oxygen species (ROS) and overexpressed antioxidant proteins. Therefore, a solution to the problems of AML treatment may be to target a broader characteristic that is common among all AML cells but is sufficiently different from normal tissues. Growing evidence indicates that AML cells, irrespective of their genetic heterogeneity, and compared to normal cells, have an increased susceptibility to the disruption of balance between pro- and anti-oxidant forces.

The most promising basis for a new strategy for treating AML is to identify leukemia-specific characteristics that are sufficiently selective to eradicate malignant cells with minimal toxicity to normal tissues. Since the cellular oxidative state is a fundamental physiological characteristic that is sufficiently different between normal hematopoietic cells and AML cells, but is shared among AML cells irrespective of intra-leukemic heterogeneity, developing agents that simultaneously target different aspects of the aberrant oxidative balance in leukemia cells could offer a plausible therapeutic option for patients.

Dimeric naphthoquinones have been reported with potent activity against acute myeloid leukemia cells. Dimeric naphthoquinones demonstrate some promising anti-neoplastic activity but very little is known about the structure activity relationships for this series. The naphthoquinone chemotype is a pharmacophore that elicits anti-cancer activity, for example in compounds such as doxorubicin and daunorubicin. The major mechanism of action for these naphthoquinones is a dramatic increase in reactive oxygen species and DNA binding. However, some dimeric naphthoquinones have limited aqueous solubility and/or require the aziridine toxicophore to elicit the anti-neoplastic activity.

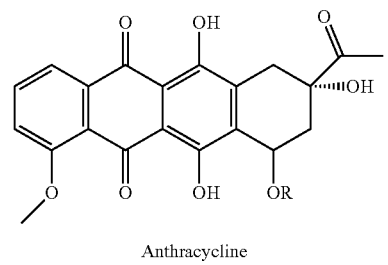

Anthracycline

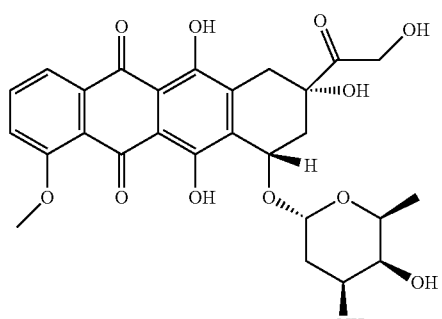

Doxorubicin

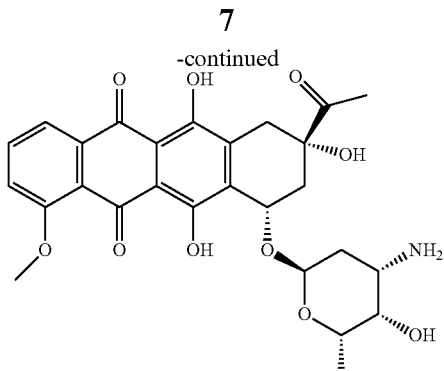

Daunorubicin

Through cyclic voltammetry studies, we have demonstrated that aziridinyl dimeric naphthoquinones can undergo a redox step, of which the cathodic and anodic peak potentials can be tuned to specifically target cellular metabolic processes. Thus, depending on the biology of oxidative states in AML cells, the electron-accepting potential of quinones can be tuned to develop rational combination regimens involving other drugs to yield selective cytotoxicity for cells with a particular redox environment.

The optimization strategy includes replacing the aziridine moiety of the compound with an amine-based solubilizing group and tuning the electronics of the naphthoquinone system by addition of an electron donating or withdrawing substituent.

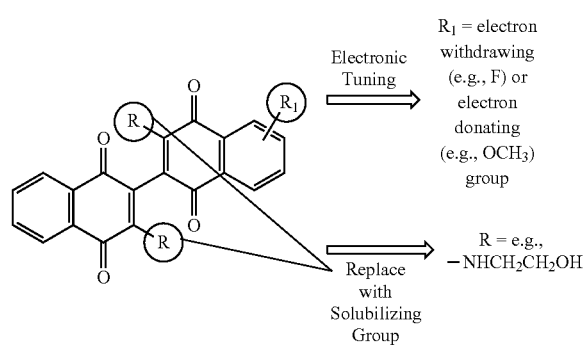

A bis-amino alcohol dimeric naphthoquinone (Compound 102, below) has been shown to prevent the proliferation of AML cell lines and primary cells from AML patients, and exhibited potent (nanomolar) inhibition of colony formation and overall cell survival in AML cells. Some preferred compounds of the invention include Compound 101, Compound 102, Compound103, Compound 104, Compound 105, and Compound 106. Any electron withdrawing groups are contemplated for use in the invention, depending on the need of the practitioner, including, for example, halides, haloalkanes, carbonyl groups, nitro groups, sulfonyl groups, and the like, preferably halides such as fluoro, chloro, bromo, and iodo. Any electron donating groups are contemplated for use in the invention as well, depending on the need of the practitioner, including, for example alkoxy, hydroxyl, amino, alkyl amino, and the like, preferably alkoxy groups such as methyloxy and ethyloxy.

Solubilizing groups suitable for use in the invention include any chemical moieties that increase solubility of the compound, and include —Cl, —Br, —I, —F, —H, —CH$_3$, —CH$_2$CH$_3$, —CH$_2$OH, —CH$_2$CH$_2$OH, —CH(CH$_2$OH)$_2$, —CH=CHOH, —CH$_2$CH$_2$(CH$_3$)OH, —CH$_2$CH(CH$_3$)CH$_2$CH$_2$OH, —CH$_2$CH$_2$OCH$_2$OH, —CH$_2$CH$_2$OCH$_2$CH$_2$OH, —CH$_2$CH$_2$OCH$_3$, —CH$_2$CH$_2$OCOCH$_3$, —CH$_2$NH$_2$, —CH$_2$N(CH$_3$)$_2$, —CH$_2$CHN(CH$_3$)$_2$, and —CH$_2$X wherein X is halo, or R$_1$ and R$_2$ can be joined to form a cyclic

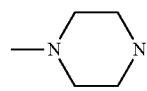

1-piperizino or

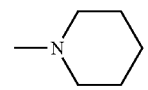

1-piperidino, which optionally is substituted at the 4-position with hydroxyl, hydroxymethyl, —CH$_2$CH$_2$OCH$_2$OH, or —CH$_2$CH$_2$OCH$_2$CH$_2$OH;

a

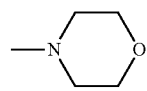

morpholino moiety, or aziridino. The R$_1$ and R$_2$ solubilizing groups can be the same or different independently. Preferred substituents include —H, —CH$_2$OH, —CH$_2$CH$_2$OH, and —CH$_2$N(CH$_3$)$_2$.

The mechanism of action for Compound 101 (structure below) is most likely production of reactive oxygen species (ROS) and double stranded DNA breaks. However, much of the activity of Compound 101 has been attributed to the aziridine moiety, a highly reactive toxicophore. The studies here related to optimizing the bis-naphthoquinone scaffold for chemical stability, improved solubility, and cytotoxicity against AML cell lines, to develop improved drugs for treatment for AML. Preferred amine dimeric naphthoquinone compounds (Compound 101, 102, 103, 104, 105, and 106) have been designed and synthesized. These compounds are designed to kill leukemia cells by dual mechanisms: (1) negatively perturbing cellular oxidative balance, and (2) effectively inhibiting IDO-1.

Compound 101

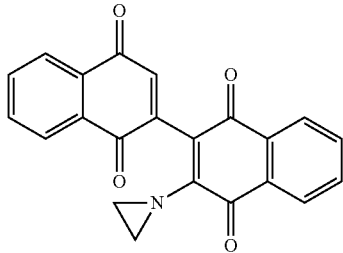

(3,3'-bis(aziridine)-2,2'-binaphthoquinone)

Compound 102

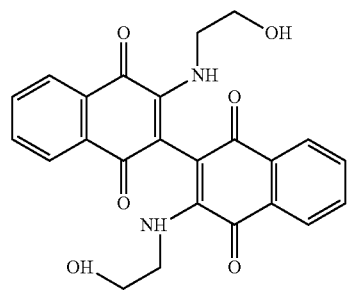

(3,3'-bis(2-aminoethanol)-2,2'-binaphthoquinone)

Compound 103

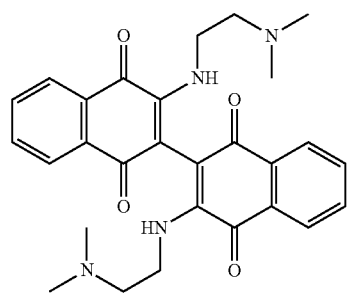

(3,3'-bis({[2-dimethylamino)ethyl]amino})-
[2,2'-binaphthalene]-1,1',4,4,'-tetrone))

Compound 104

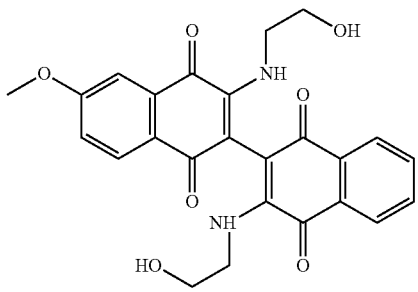

(6-methoxy, 3,3'-bis(2-aminoethanol)-2,2'-
binaphthoquinone)

Compound 105

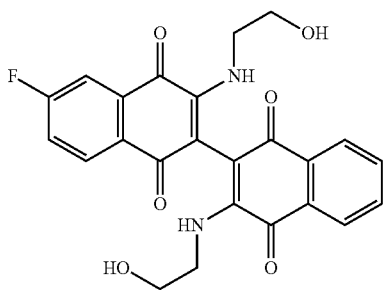

(6-fluoro, 3,3'-bis(2-aminoethanol)-2,2'-
binaphthoquinone)

Compound 106

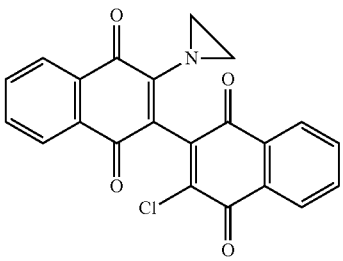

(3-(aziridin-1-yl)-3'-chloro-[2,2'-binaphthalene]-1,1'
4,4'-tetrone)

2. DEFINITIONS

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

As used herein, the term "dimeric naphthoquinone" refers to compounds having a structure according to Formula B, below, winch optionally can contain substitutions at any of the available numbered locations. These compounds also have been known as BiQ, dimeric quinones, binaphthoquinones, biquinones, bisnapthoquinones, bisquinones, oligomeric naphthoquinones, 2,2'-dimeric naphthoquinones, and are exemplified by, e.g., bis-aziridinyl dimeric naphthoquinone, halohydroxy dimeric naphthoquinone, hydroxylated dimeric naphthoquinone, halomethoxy dimeric naphthoquinone, and the like.

Formula B

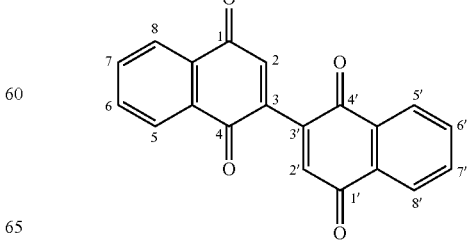

A "therapeutically effective amount" is an amount that, when administered to a subject, treats, ameliorates, and/or achieves an intended therapeutic effect, for example eliminating, reducing or mitigating a disease or condition, or a symptom of a disease or condition. This effect may be partial or temporary, and may occur only after multiple administrations or doses of the therapeutic amount.

A "subject," as used herein, is any mammal, including humans, laboratory animals, companion animals, and farm animals. The subject preferably is a human, ape, monkey, dog, cat, mouse, rat, rabbit and the like. A "subject in need" is a subject suffering from cancer or malignant/neoplastic disorders, suspected of suffering from cancer or malignant/neoplastic disorders, preferably leukemia, and more preferably acute myeloid leukemia, or from any disease condition related to or caused by a perturbation of the cellular oxidative state.

The compounds also are contemplated for use in treatment of any disease condition with local and/or systemic inflammatory conditions or related to a perturbation of the cellular oxidative state. Such disease conditions, in addition to cancer, malignant and neoplastic diseases, include but are not limited to common and devastating diseases such as autism, chronic fatigue syndrome and fibromyalgia.

The term, "treating," as used herein, means taking steps to obtain beneficial or desired results, including clinical results, such as, for example, mitigating, alleviating or ameliorating one or more symptoms of a disease; diminishing the extent of disease; delaying or slowing disease progression; ameliorating and palliating or stabilizing a metric (statistic) of disease. The effect may be prophylactic in terms of completely or partially preventing a conditions or disease or symptom thereof and/or may be therapeutic in terms of a partial or complete cure for a condition or disease and/or adverse effect attributable to the condition or disease. "Treatment" refers to the steps taken. It can include any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example causing regression of the condition or disease or symptom thereof by administering a therapeutically effective amount of the antibody.

3. OVERVIEW

Aziridinyl and other amino dimeric naphthoquinones are molecules with a new and unique chemical structure. Related compounds were rationally designed and synthesized as new anti-neoplastic agents. The results shown here indicate an in vitro activity with minimal toxicity to normal cells. An effective and modular syntheses of several amine-based dimeric naphthoquinone derivative was achieved. The compounds with solubilizing amines were chemically stable and soluble in aqueous assays. The amino alcohol moiety was preferred desirable for optimal activity.

4. EMBODIMENTS OF THE INVENTION

The compounds of the invention are dimeric naphthoquinones of Formula A:

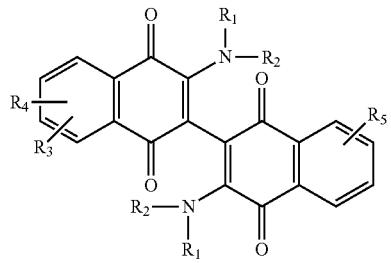

Formula A

These compounds contain $R_1$ and $R_2$ groups that tend to increase solubility of the compound, and $R_3$, $R_4$, and $R_5$ groups that are designed to modify the electronics of the naphthoquinone ring structure(s) in order to customize binding to a particular cancer cell, in particular a leukemia cell or an AML cell.

Dimeric naphthoquinones participate in the initiation and the propagation of free radical chain reactions. They are reduced to semiquinones, which are free radicals, then to hydroquinones, by one-electron reductions by different enzymes. Semiquinones can dissociate from the enzymes and be available for other reactions in the cell, and can also be synthesized non-enzymatically by the reaction between a hydroquinone and quinone and by superoxide-based oxidation of the hydroquinone anion. Because oxygen is the only other reactant, this reaction can occur as long as the hydroquinone is available in the cell.

The ability of different dimeric naphthoquinones to play a part in electron transfer reactions varies based on their structures. Through cyclic voltammetry studies, it has been discovered that dimeric naphthoquinones undergo four redox steps, of which the cathodic and anodic peak potentials can be tuned to specifically target cellular metabolic processes. For some of the dimeric naphthoquinones, cytotoxity can be predicted by redox potentials. Thus, depending on the oxidoreductases or other bases for altered electron donation present in particular cancer or neoplastic cells, particularly AML cells, the electron-accepting potential of quinones can be "tuned" to yield selective cytotoxicity for cells with a particular "redox" environment, allowing an initiation of a cascade of election transport only in cancer cells with a dysregulated redox state, and not in normal cells. This would result in a consequent increase in reactive oxygen species (ROS), producing selective cell killing.

A. Rational Design

Several dimeric naphthoquinones with potent anti-integrase activity against human immunodeficiency virus (HIV), have been reported to have cytotoxic activity against prostate and breast cancer cells. Hydroxylated dimeric, but not monomeric, naphthoquinones can inhibit clonogenicity and induce apoptosis in AML cell lines and primary cells from patients (IC50 3-5 μM) with favorable therapeutic index compared to normal hematopoietic cells. To improve the potency and bioavailability of this class of compounds, both alkylating agents and amine groups were incorporated into the quinone cores of each naphthoquinone unit. Without wishing to be bound by theory, the quinone moiety is thought to operate by perturbing cellular redox balance and its oxidation state would modulate the activity of the alkylating moiety that can form covalent bonds with a different cellular components. Here the synthesis, characterization and anti-AML activity of rationally designed dimeric naphthoquinone compounds (based on, e.g., bis-aziridine compounds) compared with bis-dimethylamine and other compounds is reported.

A crystallography study was performed, in which crystals of NAD(P)H dehydrogenase quinone 1 (NQO1) were soaked with halohydroxy dimeric naphthoquinone. At 2.9 Å resolution the study clearly showed that dimeric naphthoquinones interact with the flavin adenine dinucleotide (FAD) active site of NQO1. In addition, halohydroxy naphthoquinones are not a substrate for the transport proteins ABCB1 or ABCG2.

In a previous study, hNQO1 stored at a concentration of approximately 18-20 mg/ml in 50 mM Tris pH 8.0, 50 mM NaCl and 5 µM FAD was used for crystallization screening. Initial screening with JCSG+, Classics suite I and II from QIAGEN® resulted in initial hits in more than 20 conditions. Native data up to 2.0 Å resolution were collected using P21 crystals obtained in 20% (w/v) PEG3350 and 0.2 M ammonium citrate. Another crystal form in the space group P212121 was obtained using 20% PEG3350 and 0.2 M potassium sodium tartrate. The complex between NQO1 and E6a was obtained by soaking the P212121 native crystals in mother liquor containing 1 mM E6a. X-ray diffraction data were collected in house and at beam line 5.0.3 of the Advanced Light source at Lawrence Berkeley National Laboratory for the holo and E6a-bound hNQO1 crystals, respectively. The data were reduced using iMosflm and Aimless from the CCP4 program suite. Initial phases for both holo and E6a-bound hNQO1 were determined by molecular replacement using the program Phaser using the coordinates of an hNQO1 monomer from a previously reported holo-structure (PDB accession code: 1D4A). The initial molecular replacement solution for the hNQO1-E6a complex contained only 8 of the 14 monomers in the asymmetric unit. Using these 8 monomers as a fixed solution, the remaining monomers were placed iteratively using a combination of Phaser and Molrep. The structure was refined using Refmac5 from CCP4 program suite. Iterative cycles of model building using COOT and refinement by refmac5 and TLS- and NCS-restrained refinement using buster yielded final structures with Rwork/Rfree of 18.0/21.6 for native and 18.3/22.0 for the E6a complex. Final Structures were deposited in PDB (Accession Codes: holo-hNQO1: 5EA2, hNQO1-E6a: 5EAI). See Pidugu et al., BMC Structural Biology. 2016; 16(1):1-10.

To better understand the mechanism of action of these types of agents and the underlying biology of their therapeutic effect on perturbation of the redox stated in primary human hematopoietic cells derived from patients with AML, additional studies were perforated. The first generation compounds (without the aziridinyl moiety) induce apoptosis and increase depolarization of mitochondrial potential in AML cells. They increase oxidative stress in leukemia cells by enhancing ROS levels, which results in increased Nrf2 expression.

B. General Chemical Synthetic Methods

The synthesis of bis-amino dimeric naphthoquinones is outlined in Scheme I, below. The bis-chloride (Compound 134) was synthesized in good yield from a previously available method. Amination of Compound 134 was conducted with a series of amines, resulting in addition of either one amine group to afford the amino chlorides Formula C (e.g., Compounds 123, 124, 125, 126, and 127) or addition of two amines to form the bis-amino dimeric naphthoquinones of Formula D (e.g., Compounds 102, 103, 107, 108, 110, 111, 112, 113, 120, 121, and 122). Reagents and conditions for the reaction in scheme 1 were as follows: HNR$_1$R$_2$, DCM was 20-41% for Formula C and 3-80% for Formula D.

Compounds can be synthesized using these methods using any appropriate R$_1$ and R$_2$ groups. Suitable R$_1$ and R$_2$ groups (solubilizing) can be the same or different and include —Cl, —Br, —I, —F, —H, —CH$_3$, —CH$_2$CH$_3$, —CH$_2$OH, —CH$_2$CH$_2$OH, —CH(CH$_2$OH)$_2$, —CH=CHOH, —CH$_2$CH(CH$_3$)OH, —CH$_2$CH(CH$_3$)CH$_2$CH$_2$OH, —CH$_2$CH$_2$OCH$_2$OH, —CH$_2$CH$_2$OCH$_2$CH$_2$OH, —CH$_2$CH$_2$OCH$_3$, —CH$_2$CH$_2$OCOCH$_3$, —CH$_2$NH$_2$, —CH$_2$NHCH$_3$, —CH$_2$N(CH$_3$)$_2$, —CH$_2$CH$_2$N(CH$_3$)$_2$, —CH$_2$X, (wherein X is halo) or R$_1$ and R$_2$ can be joined to form a cyclic 1-piperizino or 1-piperidino, which optionally are substituted at the 4-position with hydroxyl, hydroxymethyl, —CH$_2$CH$_2$OCH$_2$OH, or —CH$_2$CH$_2$OCH$_2$CH$_2$OH, or a morpholino or aziridino moiety. The —CH$_2$CH$_2$OH and —CH$_2$CH$_2$N(CH$_3$)$_2$ groups are preferred.

Scheme 1. Synthesis of bis-amino dimeric naphthoquinones.

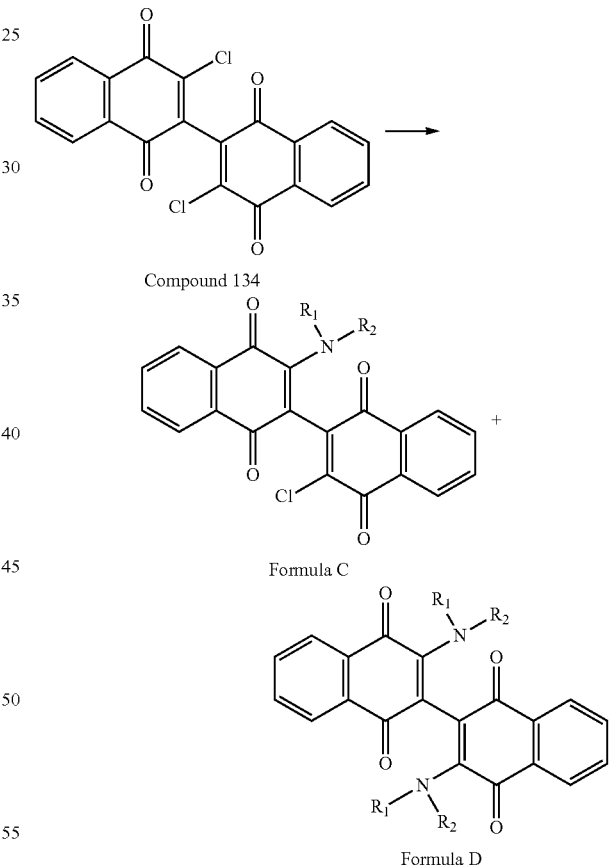

Incorporation of substituents on the phenyl ring of the naphthoquinone was accomplished by starting with either the 7-substituted tetralone of Formula E (e.g., Compound 140, 7-methoxy substitution or Compound 141, 7-fluoro substitution) as outlined in Scheme 2, below. Oxidation of these tetralones in the presence of dithenium decacarbonyl produced 2-hydroxy naphthoquinones of Formula F (e.g., Compounds 142 and 143). Coupling of the substituted 2-hydroxy naphthoquinones with 2,3-dichloronaphthoquinone produced the dimeric 2-chloro-2'-hydroxy naphthoquinones of Formula G (e.g., Compounds 135 and 136) in good yield. Chlorination with thionyl chloride produced the dichlorides of Formula H (e.g., Compounds 137 and 138). Amination with 2-aminoethanol resulted in the desired hydroxyethyl amines of Formula I (e.g., Compounds 104 and 105).

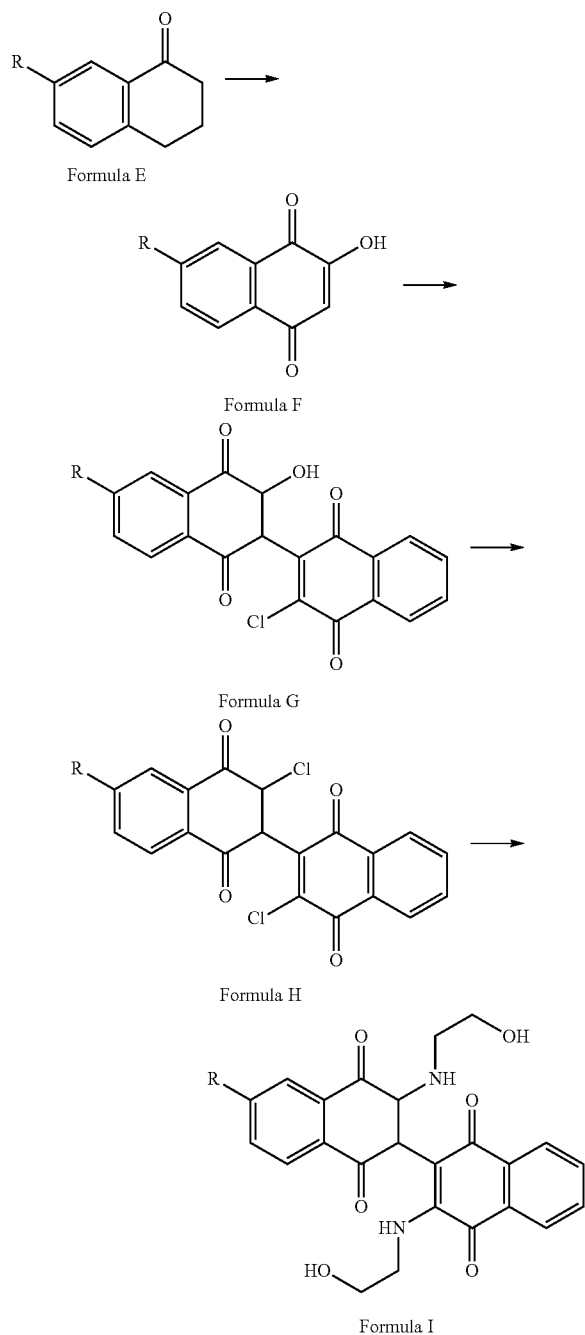

Scheme 2. Exemplary Incorporation of Substituents into Naphthoquinones.

Formula E

Formula F

Formula G

Formula H

Formula I

See FIG. 1 for the detailed chemical synthetic scheme 3. Formula E is Compound 140 when R=OMe and Compound 141 when R=F; Formula F is Compound 142 when R=OMe and Compound 143 when R=F; Formula G is Compound 135 when R=OMe and Compound 136 when R=F; Formula H is Compound 137 when R=OMe and Compound 138 when R=F; Formula I is Compound 104 when R=OMe and Compound 105 when R=F.

Reagents and conditions for scheme 3 were as follows. a: $Re_2(CO)_{10}$, $O_2$, dioxane, 20% for Compound 142, 14% for Compound 143; b: 2,3-dichloronaphthoquinone, $Cs_2CO_3$, $CH_3CN$, 68% for Compound 135; 62% for Compound 136; c: $SOCl_2$, 60% for Compound 137; 56% for Compound 138; d: 2-aminoethanol, DCM, 23% for Compound 104; 28% for Compound 105.

C. Additional Design and Synthesis

Amination of the dichloro dimeric naphthoquinone Compound 134, was accomplished by treatment with limiting and excess amounts of aziridine to produce mono- and bis-aziridinyl dimeric naphthoquinone, Compounds 106 (3-(aziridin-1-yl)-3'-chloro-[2,2'-binaphthalene]-1,1' 4,4'-tetrone) and Compound 101 (3,3'-di(aziridin-1-yl)-[2,2'-binaphthalene]-1,1 4,4'-tetrone), or excess dimethylamine to produce bis-dimethylamino dimeric naphthoquinone, Compound 114 (3,3'-bis(dimethylamino)-[2,2'-binaphthalene]-1,1',4,4'-tetrone)(see scheme 4, below). Compounds 106 and Compound 101 were isolated in 49% and 44% yield, respectively, by dropwise addition of aziridine to a solution of 3,3'-dichloro-[2,2'-binaphthalene]-1,1',4,4'-tetrone (Compound 134) in anhydrous tetrahydrofuran (THF) at room temperature with stirring for 16-20 hours. Initial gentle warming (35° C.) was required to complete dissolution of Compound 134.

The dichioro dimeric naphthoquinone (Compound 134) was synthesized according to the literature. Aziridine was used at 2 and 6 equivalents concentration of Compound 134 for synthesis of mono- and bis-aziridinyl dimeric naphthoquinones, respectively. The next day, the reaction mixture was partitioned between $CH_2Cl_2$ and water. The organic layer was collected, washed with water twice and then brine, dried using $Na_2SO_4$, filtered and concentrated. The residue was adsorbed onto silica gel in the cold and chromatographed over silica gel using a Biotage Isolera® running with a gradient of ethyl acetate in hexane to provide the title Compound 114 as an orange red solid.

To demonstrate the influence of the aziridine moiety on the naphthoquinone core for antileukemic activity, Compound 114 (3,3'-bis(dimethylamino)-[2,2'-binaphthalene]-1,1',4,4'-tetrone), which in theory, cannot undergo a nucleophilic attack by DNA, was synthesized. Compound 114 is the isostere of bis-aziridine dimeric naphthoquinone, with similar electronics and size characteristics, but without the akltaing moiey. As shown in Scheme 4, in a pressure tube and in presence of N,N-diisopropylethylamine, dimethylamine hydrochloride was added to Compound 134, and the solution was stirred in dichloromethane for 48 hours. After removing all volatile materials in the reaction solution in vacuo, the crude solid was preabsorbed onto silica gel and chromatographed in 75% EtOAc/hexanes to 100% EtOAc. The purified product was triturated with hexanes and ether (1:1, 5 mL), and the final dark red product was collected by filtration in 48% yield.

Scheme 4. Synthesis of mono- and bis-aziridinyl and bis-dimethylamino dimeric naphthoquinones.

Scheme 4. Synthesis of mono- and bis-aziridinyl and bis-dimethylamino dimeric naphthoquinones.

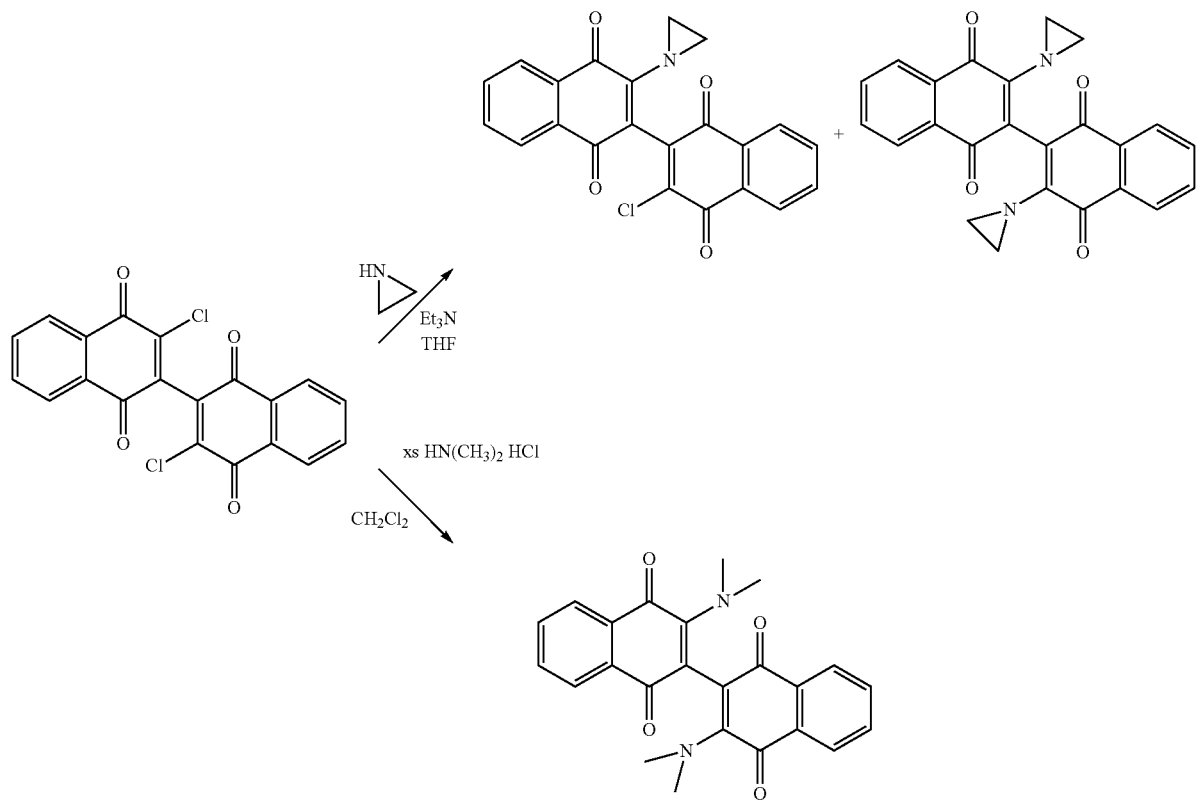

Compound 106; Aziridine (21 μL, 0.4 mmol, 2 equiv), 1 (76 mg, 0.2 mmol, 1 equiv), THF, RT, 12 h, 49%; $^1$H-NMR (400 MHz, CDCl$_3$): δ 8.28-8.26 (m, 1H, Ar), 8.18-8.15 (m, 2H, Ar), 8.11-8.09 (m, 1H, Ar), 7.84-7.82 (m, 2H, Ar), 7.76-7.74 (m, 2H, Ar), 2.33, 2.26 (Aziridine, 4H, CH$_2$CH$_2$, J$_{AB}$=6.2 Hz); $^{13}$C-NMR:(100 MHz, d$_6$-DMSO) 181.4, 181.2, 180.5, 177.1, 154.9, 144.9, 141.5, 135.4, 135.2, 135.1, 134.2, 131,9, 131.7, 131.6 (2), 127.6, 127.4, 126.8, 126.2, 121.5, 28.5 (2); MS (ESI) m/z calculated for C$_{22}$H$_{12}$ClNO$_4$ (M$^+$): 389.1, found: 390.0 (M+H$^+$).

Compound 101; Aziridine (63 μL, 1.2 mmol, 6 equiv), 1(76 mg, 0.2 mmol, 1 equiv), Et$_3$N (84 mL, 0.6 mmol, 3 equiv), THF, RT, 16 h, 44%; $^1$H-NMR (400 MHz, CDCl$_3$): δ 8.16-8.11 (m, 4 H, Ar), 7.75-7.73 (m, 4H, Ar), 2.31-2.26 (m, 8H, 2×CH$_2$CH$_2$); $^{13}$C-NMR (100 MHz, d$_6$-DMSO): 182.5, 180.9, 154.3, 134.8, 133.8, 132.5, 131.7, 126.5, 126.2, 122.9, 20.5; MS (ESI) m/z calculated for C$_{24}$H$_{16}$N$_2$O$_4$ (M$^+$): 396.1, found: 397.0 (M+H$^+$).

Compound 114: Dimethylamine hydrochloride (0.329 g, 4.03 mmol), 1 (0.218 g, 0.569 mmol), N,N-diisopropylethylamine (0.7 mL), CH$_2$Cl$_2$ (10 mL), pressure tube, RT, 48 h; 48%; $^1$H-NMR (400 MHz, DMSO-d$_6$) δ 8.01-7.99 (d, 2H,Ar), 7.91(d, 2H, Ar), 7.81-7.78 (m, 4H,Ar), 2.89 (s, 12H); MS (ESI) m/z calculated for C$_{24}$H$_{20}$N$_2$O$_4$) (M$^+$): 400.1, found: 401.1 (M+H$^+$).

D. In Vitro Cellular Studies

Initial efforts into the substitution of the dimeric naphthoquinones were undertaken to improve the aqueous solubility and potentially the potency over the parent 3-chloro-3'-hydroxy dimeric naphthoquinone (Compound 144).

Addition of an amino or amino-alcohol groups onto the dimeric naphthoquinone core moderately improved the activity against MOLM14 and MV411 cells in every instance with the hydroxyl ethyl piperazine compound (Compound 126) showing the greatest improvement (See Table 1, below).

TABLE 1

Cellular Activity of 2-chloro-2'-amino Dimeric Naphthoquinones.

| Compound | R-group | MOLM14 IC50 (μM) | MV411 IC50 (μM) |
|---|---|---|---|
| 144 (reference) | —OH | 6.5 ± 0.28 | 3.0 ± 0.07 |
| 123 | 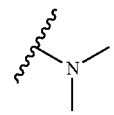 | 3.0 ± 1.42 | 2.4 ± 2.0 |

TABLE 1-continued

Cellular Activity of 2-chloro-2'-amino Dimeric Naphthoquinones.

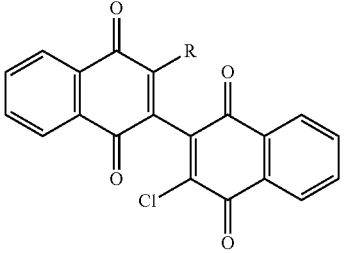

| Compound | R-group | MOLM14 IC50 (μM) | MV411 IC50 (μM) |
|---|---|---|---|
| 124 | 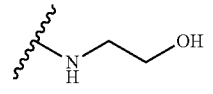 [SMILES: *NCCO] | 2.8 ± 0.01 | 1.3 ± 1.0 |
| 125 | 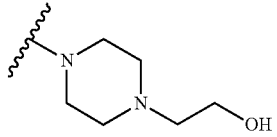 [SMILES: *N1CCN(CCO)CC1] | 2.2 | 1.2 |
| 126 | 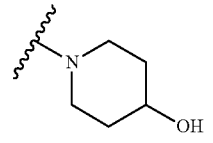 [SMILES: *N1CCC(O)CC1] | 0.85 ± 0.25 | 0.76 ± 0.36 |
| 127 | 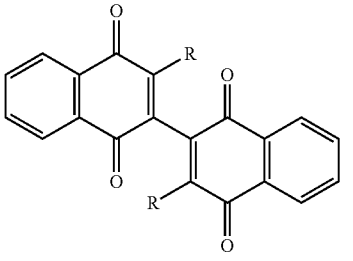 | 3.6 ± 0.63 | 2.1 ± 0.56 |

Replacing the 3'-chlorine with another amino group resulted in 3-, 3'-diamino dimeric naphthoquinones as shown in Table 2, below. The bis N,N-dimethyl amino derivative Compound 120 demonstrated no improvement in cellular activity over the mono-amine Compound 123. Likewise, the bis-4-hydroxypiperidine derivative Compound 122 offered no improvement over the monoamine Compound 127. The bis-hydroxyethyl piperazine derivative. Compound 121 was actually slightly less potent in both cell lines than its corresponding mono-amine derivative Compound 126. By far, the greatest improvement was noted with the bis-N, N,N-trimethylaminoethyl derivative Compound 103 and the bis-amino alcohol derivative Compound 102, both of which demonstrated marked improvement over the analogous mono-amine derivatives Compound 124 and Compound 125. This represents an increase in cellular potency by order of magnitude over the mono-amines.

TABLE 2

Cellular Activity of 2-, 2'-Diamino Dimeric Naphthoquinones.

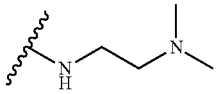 [SMILES: *NCCN(C)C]

| Compound Number | R-group | MOLM14 IC50 (μM) | MV411 IC50 (μM) |
|---|---|---|---|
| Compound 102 | 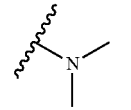 | 0.16 ± 0.01 | 0.2 ± 0.20 |
| Compound 103 | 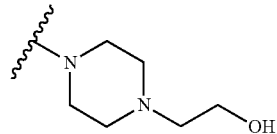 [SMILES: *N1CCN(CCO)CC1] | 0.12 | 0.49 |
| Compound 120 | 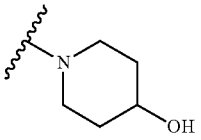 | 2.8 ± 0.91 | 2.15 ± 0.64 |
| Compound 121 | | 1.17 | 1.65 |
| Compound 122 | | 4.3 ± 2.12 | 2.5 |

Further improvements to potency were attempted. Some compounds closely related to Compound 102 were synthesized and analyzed as outlined in Table 3, below. Addition of a methyl group on the nitrogen (Compound 107) or on both the nitrogen and oxygen (Compound 108) resulted in dramatic loss of potency in both cell lines. Similarly, acetylation of the alcohol of Compound 102 resulted in loss of potency as demonstrated by Compound 109. Taken together, these results emphasize the importance of the alcohol and secondary amine. Extending the alcohol away from the naphthoquinone core also resulted in loss of potency in both cell lines as demonstrated by Compounds 110 and 111. Even subtle changes to the two carbons between the amine and alcohol resulted in an order of magnitude loss in potency as demonstrated by Compounds 112 and 113. In addition, subtle changes to the naphthoquinone core by addition of an electron donating (e.g. methoxy derivative Compound 104) or an electron withdrawing group (e.g. fluorine derivative Compound 105) resulted in loss of potency over Compound 102.

TABLE 3

Derivatives of Compound 102.

| Compound | Structure | MOLM14 IC50 (μM) | MV411 IC50 (μM) |
|---|---|---|---|
| 102 | 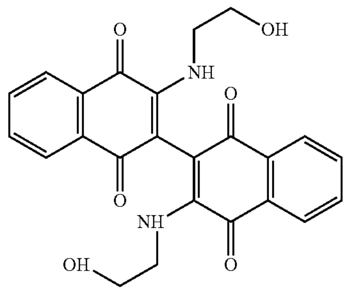 [SMILES: O=C1C(NCCO)=C(C2=C(NCCO)C(=O)c3ccccc3C2=O)C(=O)c2ccccc21] | 0.16 ± 0.01 | 0.2 ± 0.20 |
| 104 | 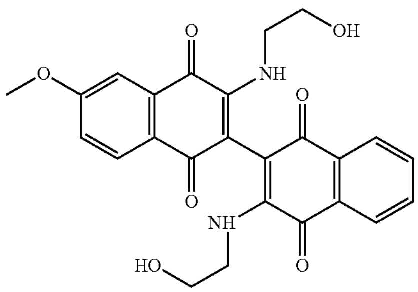 [SMILES: COc1ccc2c(c1)C(=O)C(NCCO)=C(C1=C(NCCO)C(=O)c3ccccc3C1=O)C2=O] | 0.37 ± 0.17 | 1.16 ± 0.2 |
| 105 | 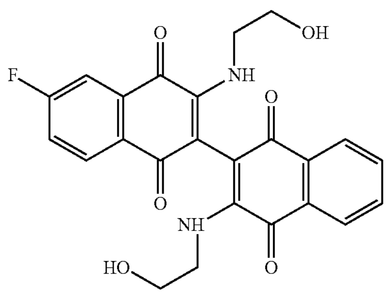 [SMILES: O=C1C(NCCO)=C(C2=C(NCCO)C(=O)c3cc(F)ccc3C2=O)C(=O)c2ccccc21] | 1.3 ± 0.23 | 2.05 ± 0.40 |
| 107 | 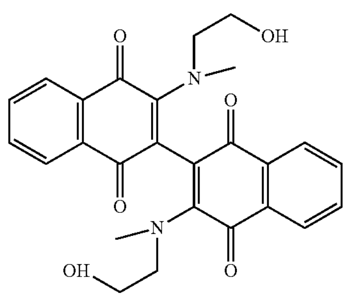 [SMILES: CN(CCO)C1=C(C2=C(N(C)CCO)C(=O)c3ccccc3C2=O)C(=O)c2ccccc2C1=O] | 5.85 ± 0.64 | 5.25 ± 0.35 |
| 108 | 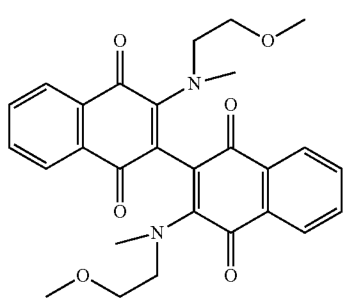 [SMILES: COCCN(C)C1=C(C2=C(N(C)CCOC)C(=O)c3ccccc3C2=O)C(=O)c2ccccc2C1=O] | 5.55 ± 0.78 | 5.5 ± 0.71 |

TABLE 3-continued

Derivatives of Compound 102.

| Compound | Structure | MOLM14 IC50 (μM) | MV411 IC50 (μM) |
|---|---|---|---|
| 109 | 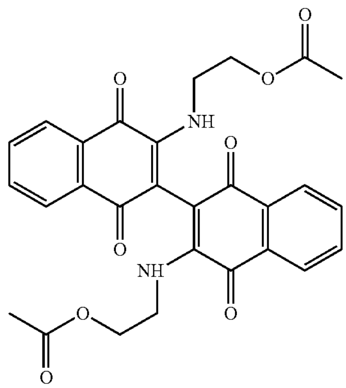 [SMILES: CC(=O)OCCNC1=C(C2=C(NCCOC(C)=O)C(=O)c3ccccc3C2=O)C(=O)c2ccccc2C1=O] | 1 | 2.2 ± 0.74 |
| 110 | 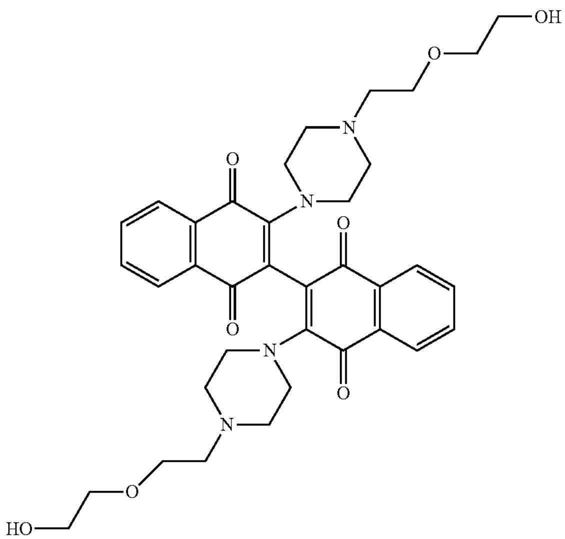 [SMILES: O=C1C(C2=C(N3CCN(CCOCCO)CC3)C(=O)c3ccccc3C2=O)=C(N2CCN(CCOCCO)CC2)C(=O)c2ccccc21] | 1.90 ± 0.32 | 140 ± 0.91 |
| 111 | 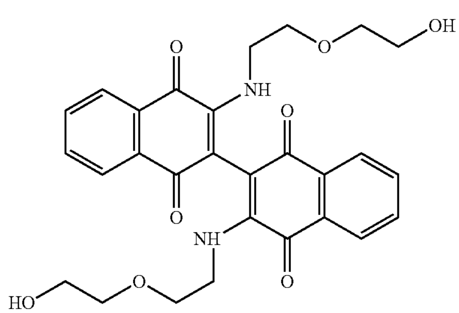 [SMILES: O=C1C(NCCOCCO)=C(C2=C(NCCOCCO)C(=O)c3ccccc3C2=O)C(=O)c2ccccc21] | 0.75 | 1.45 |

TABLE 3-continued

Derivatives of Compound 102.

| Compound | Structure | MOLM14 IC50 (µM) | MV411 IC50 (µM) |
|---|---|---|---|
| 112 | 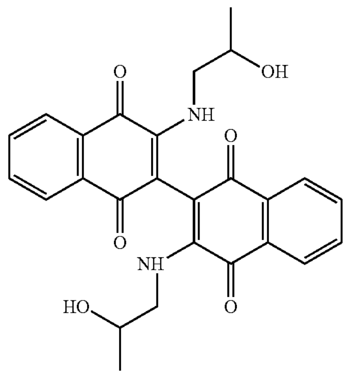 [SMILES: CC(O)CNC1=C(C2=C(NCC(C)O)C(=O)c3ccccc3C2=O)C(=O)c2ccccc2C1=O] | 1.49 ± 0.46 | 3.94 ± 2.23 |
| 113 | 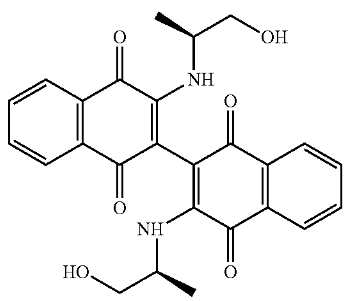 [SMILES: C[C@@H](CO)NC1=C(C2=C(N[C@@H](C)CO)C(=O)c3ccccc3C2=O)C(=O)c2ccccc2C1=O] | ND | ND |

E. Therapeutic Agents and Compositions

The compounds discussed herein can be present in the form of pharmaceutically acceptable salts, acids, hydrates, and solvates, or as a base. These compounds can exist in amorphous form or in any crystalline form.

Any pharmaceutically acceptable salt of the compound can be used, as may be convenient. Generally, these salts are derived From pharmaceutically and biologically acceptable inorganic or organic acids and bases or metals. Examples of such salts include, but are not limited to: acetate, adipate, alginate, ammonium, aspartate, benzoate, benzenesulfonate (besylate), bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, methanesulfonate (mesylate), 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts.

The therapeutic agents of some embodiments of the inventive compounds also are meant to include any or all stereochemical forms of the therapeutic agents (i.e., the R and/or S configurations for each asymmetric center). Therefore, single enantiomers, racemic mixtures, and diastereomers of the therapeutic agents are within the scope of the invention. Also within the scope of the invention are steric isomers and positional isomers of the therapeutic agents.

The therapeutic agents of some embodiments are also meant to include compounds which differ only in the presence of one or more isotopically enriched atoms. For example, therapeutic agents in which one or more atom is replaced by, for example, deuterium, tritium, $^{13}C$, $^{14}C$ (or any isotopic labels as commonly used in the art such as phosphorus, calcium, iodine, chlorine, bromine, or any other convenient element for isotopic labeling) are within the scope of this invention.

The compounds of this invention are useful in the treatment of disease, and therefore are contemplated for incorporation into pharmaceutical compositions. Preferably, the pharmaceutical compositions comprise a therapeutically effective amount, however the composition or dosage form can comprise a partial therapeutically effective amount when it is designed to administer multiple doses to make up a therapeutic amount.

In a preferred embodiment, the therapeutic agents of some embodiments are administered as a pharmaceutical composition that includes a pharmaceutically acceptable carrier or vehicle. The terms "pharmaceutically acceptable carrier" or "pharmaceutically acceptable vehicle" refer to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, semi-solid, liquid, or gaseous carriers known in the art, such as those discussed in the art. Suitable carriers depend on the route of administration contemplated for the pharmaceutical composition. Such routes can be any route which the practitioner deems to be most effective or convenient using considerations such as the patient, the patient's general condition, and the specific condition to be treated.

A non-inclusive list of carriers and vehicles contemplated for use with the invention follows: containers, fillers, adjuvants, buffers, binders, lubricants, diluents, surfactants, dispersing agents, pH adjusters, preservatives, antibacterial agents, antioxidants, chelating agents, flavorings, colorings, taste-masking agents, sweeteners, emulsifiers, suspending agents, wetting agents, and the like, including coatings and various means and devices for producing delayed or timed release of the compound.

Specific solid carriers can include, for example, starch (e.g., corn starch, potato starch, and the like), cellulose or modified cellulose and methylcellulose (e.g., microcrystalline cellulose, and the like), sugars (e.g., lactose, sucrose, glucose, and the like), clays, minerals (e.g., talc, and the like), gums, magnesium stearate, and the like.

Routes of administration contemplated for compounds of the invention include any route known in the art which is convenient to the practitioner or the subject. Such routes include oral, buccal, nasal, transmucosal, sublingual, topical, transdermal, subcutaneous, rectal, vaginal, inhalation, intravenous, intraarterial, intrathecal, intraperitoneal, local injection, by infusion, by depot, wound covering, or any suitable route. Thus, the dosage form or pharmaceutical composition is tailored for the particular contemplated route of administration, as is known in the art and common in the pharmaceutical and medical arts.

Therefore, the forms which the pharmaceutical composition can take will include, but are not limited to: tablets, capsules, caplets, lozenges, dragees, pills, oral solutions, powders for dilution, powders for inhalation, vapors, gases, granules, sterile solutions for injection, transdermal patches, buccal patches, inserts and implants, rectal suppositories, vaginal suppositories, creams, lotions, ointments, oils, gels, suspensions, emulsions, topical coverings (e.g., would coverings and bandages, and the like), and the like as are needed or desired for the route of administration chosen.

F. Therapeutic Applications

The compounds and compositions of the invention can be used for treatment of cancer, leukemias, and in particular acute myeloid leukemia. In addition, the invention is contemplated for use treating diseases and conditions wherein there is a perturbation or malfunction in the cellular oxidative state. Any such condition or disease is contemplated, however, conditions such as autism, chronic fatigue syndrome and fibromyalgia, all of which are associated with local and systemic inflammatory conditions and mitochondrial malfunction related to perturbation of cellular oxidative state, are preferred.

The compounds and compositions can be used in combination therapies as well. Therefore, it is contemplated that the compounds and compositions can be used together with a second agent, preferably one or more agent that is useful in the treatment of the same disease or condition. Examples of such agents, which can be used or have been used in the treatment of AML are Cytarabine, Daunorubicin, Daunomycin, Idarubicin, mitoxantrone, Cladribine, Fludarabine, Topotecan, Etoposide, 6-thioguanine, Hydroxyurea, Methotrexate, 6-mercaptopurine, Azacitidine, and Decitabine. Therefore, the compounds of this invention can be combined into one pharmaceutical composition with the second agent or agents, or the two or more compounds can be given in separate pharmaceutical compositions G. Dosage and Administration The pharmaceutical compositions of the invention are designed and sized to provide convenient therapeutic amount or partial therapeutic amount. Therefore, preferably a dosage form contains an amount of the inventive compound in the range of about 5-150 mg/m$^2$, preferably about 10-90 mg/m$^2$, and most preferably about 45-60 mg/m$^2$ (including about 45 mg/m$^2$, 50 mg/m$^2$, 55 mg/m$^2$ or 60 mg/m$^2$ to the subject.

H. Discussion

Molecules that can relatively selectively augment oxidative stress and directly damage DNA in rapidly proliferating AML cells can be a promising approach to developing safe and effective compounds for treating AML. To this end, a unique dimeric amino-naphthoquinone, which possesses aziridine groups was designed and tested it against AML cells. The dimeric naphthoquinones showed a potent anti-leukemic effect with a favorable therapeutic index when compared with normal hematopoietic cells and was well tolerated in in vivo animal studies. The findings here are innovative in at least two respects.

First, exploitation of the cellular oxidative state and its aberrancy in AML cells with novel dimeric naphthoquinones have been demonstrated, through cyclic voltammetry studies, that these dimeric naphthoquinones can undergo four redox steps, of which the cathodic and anodic peak potentials can be tuned to specifically target cellular/metabolic processes. For some of the naphthoquinones, cytotoxicity could be predicted by redox potentials. Participating in redox cycling generates significant levels of ROS which may contribute to the cytotoxicity of the compounds.

Second, the specific dimeric naphthoquinone derivative, i.e. Compound 101, simultaneously carries unique properties, each of which targets different fragments of AML cells allowing, in theory, no alternative mechanism to escape cell death. Bis-aziridinyl dimeric naphthoquinones are amino-naphthoquinones possessing a cyclic amino group (aziridine) in the 2-position of the 1,4-naphthoquinone moiety. The heterocyclic nitrogen atom at this position empowers (1) geometric modification of the molecules and their reduction intermediates and (2) modulation of the substituent's effects on the electronic properties of the quinone system. In addition, the presence of the aziridine group provides a classical DNA alkylator, causing inter- and intra-strand DNA cross link.

Further, studies should include exploration of the chemistry of halogenated and hydroxylated nitro-dimeric naphthoquinones in organic synthesis and application of this chemistry to the systems so that properties can be developed to efficiently integrate in vivo, in vitro, structural, and biochemical properties. Depending on the oxidoreductases or other bases for altered electron donation present in AML cells, the electron-accepting potential of quinones could in principle be tuned to yield selective cytotoxicity for cells with a particular redox environment, allowing initiation of a cascade of electron transport only in AML cells, which have a dysregulated redox state, and not in normal cells, resulting in an increase in ROS and producing selective cell killing.

5. EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1. Materials and Methods

A. General Methods

All solvents were reagent grade or HPLC grade. Unless otherwise noted, all materials were obtained from commercial suppliers and used without further purification. $^1$H NMR spectra were recorded at 400.16 MHz. All $^{13}$C spectra were recorded at 100.63 MHz. The HPLC solvent system consisted of distilled water and acetonitrile, both containing 0.1% formic acid.

Analytical LC/MS was performed on an Agilent® 1200 series HPLC system equipped with an Agilent® G1315D DAD detector (detection at 220 nm) and an Agilent® 6120 quadrupole MS detector. The analytical HPLC conditions used a gradient of 20% acetonitrile/80% water for 0.5 minutes followed by an increase to 85% acetonitrile/15% water over 4 minutes and continuation of 85% acetonitrile/15% water for 3.5 minutes with a Luna® $C_{18}$ column (2.1 mm Å~50 mm, 3.5 μm) at a flow rate of 0.75 mL/minute. All final compounds tested were confirmed to be of ≥95% purity by the HPLC methods described above.

B. Chemicals, Reagents, and Purification

For the synthesis of amino dimeric naphthoquinones, all solvents were reagent or high performance liquid chromatography (HPLC) grade. Unless otherwise noted, all materials were obtained from commercial suppliers and used without further purification. $^1$H NMR spectra were recorded at 400 MHz. The HPLC solvent system consisted of distilled water and acetonitrile, both containing 0.1% formic acid. Preparative HPLC purification was performed on an Agilent® 1200 series HPLC system equipped with an Agilent® G131SD DAD detector using a Phenomenex Luna® 5 μm C18 column (21.2 mm Å 250 mm, 5 μm). Analytical HPLC was performed on an Agilent® 1200 series HPLC system equipped with an Agilent® G1315D DAD detector (detection at 220 nm) and an Agilent® 6120 quadrupole MS detector. The analytical HPLC conditions involve a gradient of 20% acetonitrile/80% water for 0.5 minutes followed by an increase to 85% acetonitrile/15% water over 4 minutes and continuation of 85% acetonitrile/15% water for 3.5 minutes with a Luna® C18 column (2.1. mm Å~50 mm, 3.5 μm) at a flow rate of 0.75 mL/min. All final compounds tested were confirmed to be of ≥95% purity by the HPLC methods described above.

C. Cell Lines and Culturing

Human AML MOLM-14 cells and THP-1 (FLT3 wild type) cells are commercially available and can be purchased from ATCC (ATCC, Manassas, Va.). For some of the studies reported here, the human AML cells (MOLM-14 and MV4-11) were the kind gift of Dr. Mark Levis from Johns Hopkins University. Both of these cell lines carry the fms-like tyrosine kinase 3 internal tandem duplication (FLT3-ITD) mutation. The human AML cells, THP-1, were purchased from American Type Culture Collection (ATCC, Manassas, Va., USA). THP-1 cells carry wild type FLT3 (FLT3-WT). Primary human leukemia cells were obtained through the institutional (Institutional Review Board (IRB) approved) Tumor and Cell procurement Bank at the University of Maryland. The morphological, cytogenetics and mutational characteristics of each primary AML cells are reported in Example 5, below.

Viable cell number counts were obtained using trypan blue exclusion. Cell lines were grown at 37° C. with 5% $CO_2$ atmosphere with RPMI 1640 (Life technologies, Carlsbad, Calif.) supplemented with heat-inactivated 10% (VN) fetal bovine serum. Cell lines were grown and maintained according to ATCC recommendations.

Bone marrow aspirate or whole blood samples were received in sodium ethylenediaminetetraacetate (EDTA) tubes, and diluted 1:1 with phosphate-buffered saline (PBS). Cells were isolated from diluted samples by density separation in lymphocyte separation medium (Corning Cell-gro®) with centrifugation at 400×g for 30 minutes with no brake. Cells from healthy donor whole blood were isolated in similar manner. N01mal bone marrow mononuclear cells (NBM) were purchased from Lonza®. Viable cell numbers were calculated using trypan blue exclusion. All primary AML cells and cell lines were grown in 37° C. with 5% $CO_2$ atmosphere in Roswell Park Memorial institute (RPMI) 1640 medium (Life Technologies®) supplemented with heat-inactivated 10% (v/v) fetal bovine serum. Cell lines were grown and maintained according to ATCC recommendations.

D. JC50 Proliferation Assay

Cell lines were seeded into 96-well plates the afternoon prior to treatment. Approximately 18 hours later, bis and mono-aziridine dimeric naphthoquinone compounds were semi-serially diluted in dimethyl sulfoxide (DMSO) and then growth medium, and added to cells. Plates were incubated for 72 hours prior to addition of WST-1 (Promega®). Plates were read after 4 additional hours of incubation at 37° C. using a Bio-Tek Synergy® HT plate reader (Bio-Tek®). Data were analyzed and graphed using GraphPad Prism® Software (Graph Pad®).

E. Cell Survival Assays

MOLM-.14 and THP-1 cells were seeded in 96-well plates and treated with DMSO, mono- and bis-aziridinyl dimeric naphthoquinone compounds, or dimethylamine dimeric naphthoquinone Compound 114 as previously described. Cells were incubated for 72 hours, and then counted using trypan blue exclusion on the Countess® automated cell counter (Life Technologies®). Cell counts were performed in duplicates, and the averages were graphed using GraphPad Prism® software (GraphPad®).

F. Clonogenic Assays

MOLM-14 and THP-1 were treated with either DMSO control or mono-aziridine dimeric naphthoquinone or bis-aziridinyl dimeric naphthoquinone compounds at concentrations of 0.1, 1, 10 and 100 μM (micromolar) for 24 hours. The cells then were washed with growth medium and resuspended in growth medium and methylcellulose with or without DMSO or the treatment compounds. After 7 or 13 days (MOLM-14 or THP-1, respectively), treatment was terminated by addition of 1.0 mg/mL, iodonitrotetrazolium chloride (INT; Sigma Aldrich®) and read 24 hours later with an automated colony counter (Symbiosis®). Data were analyzed and graphed using GraphPad Prism® software.

G. Cell Proliferation Assay

Primary AML cells from patients and cell lines were seeded into 96-well plates the afternoon prior to treatment. Eighteen hours later, amino-dimeric naphthoquinone Compounds 106, 101, and 114 were semi-serially diluted in dimethyl sulfoxide (DMSO) and then growth medium, and added to the cells. In order to quantitate proliferation of metabolically active cells, plates were incubated for 72 hours for cell lines and 48 hours for primary AML cells prior to addition of water-soluble tetrazolium (WST-1) (Clontech®). Plates were read after four additional hours of incubation at 37° C. using a Bio-Tek Synergy® HT plate reader (Bio-Tele®). Data were analyzed and graphed using GraphPad Prism® Software (GraphPad®). IC50 was defined as the concentration that decreases viable cell numbers by 50%. IC50 values were calculated as mean±standard deviation from at least two independent experiments. If availability of primary blasts was limited, the IC50 was obtained from a single experiment.

H. Measurement of Cellular Reactive Oxygen Species (ROS)

MOLM-14 and THP-1 cells in logarithmic growth phase were centrifuged and resuspended in PBS at one million cells per milliliter (mL) of medium. Cells were preloaded with 2',7'-dichlorodihydrofluorescein diacetate (H2DCFA, Life Technologies®) at a final concentration of 2 μM and incubated at 37° C. in the dark for 25 minutes. Cells were centrifuged and resuspended at one million per mL in phenol red-free RPMI plus 10% FBS and incubated at 37° C. in the dark for 25 minutes. Treatments were prepared at 2x concentrations of 40, 20, 4 or 1 μM in complete phenol red-free RPMI and added to each well to yield 1x concentrations of 20, 10, 2, or 0.5 μM. Cells were incubated in the dark at 37° C. and measurement of ROS was performed with a Bio-tek® Synergy HT plate reader at various time points post treatment.

I. Gamma-H2Ax Immunofluorescence Assay

MOLM-14 cells were seeded in the afternoon and the following morning treated with DMSO, or aziridinyl-dimeric naphthoquinone Compound 101 at 1x, 5x; or 10x IC50 concentrations. Cells were harvested at 24 and 48 hours. Briefly, cells were washed twice with PBS, counted, and resuspended into PBS/2% FBS. Approximately 150,000 cells were pelleted on Superfrost® microslides (Thermo Fisher Scientific®) using a cytospin machine (Thermo Fisher Scientific®) for 10 minutes at 800 RPM. Slides were air-dried for 5 minutes, then fixed in 4% paraformaldehyde for 15 minutes, washed with PBS 3 times, each time for 5 minutes and permeabilized with permeabilization buffer (50 mM NaCl, 3 mM $MgCl_2$, 10 mM HEPES, 200 mM sucrose, and 0.5% Triton-X-100) for 10 minutes. After overnight blocking in PBS/10% FBS, slides were washed 3 times, each time for 5 minutes with wash buffer (PBS, 1% BSA, and 0.1% Triton-X-100), stained with 1:100 anti-phosphohistone H2Ax antibody (Millipore®), washed with wash buffer again 3 times, each time for 5 minutes, and stained with 1:200 goat anti-mouse IgG, Dylight 594® (Thermo Scientific®), washed 3 times, each time for 5 minutes with wash buffer, and mounted with Vectashield® mounting medium with 4',6-diamidino-2-phenylindole (DAPI, Vector Labs®). Slides sat overnight and were sealed the following day with clear nail polish.

Example 2. Specific Chemical Synthetic Methods 3-chloro-3'-(dimethylamino)-2,2'-binaphthalenyl-1,1',4, 4'-tetrone (Compound 123).

In a pressure tube, 3,3'-dichloro-[2,2'-binaphthalene]-1,1', 4,4'-tetrone 6 (0.190 g, 0.496 mmol), dimethylamine hydrochloride (0.047 g, 0.576 mmol), and DIEA (0.5 mL) were stirred in 8 mL of dichloromethane for 30 hours. All volatile solvents from the reaction solution were removed in vacuo. The crude solid was preabsorbed onto silica gel and chromatographed in 75% EtOAc/hexanes→100% EtOAc. The purified product then was triturated with hexanes and ether (1:1, 5 mL), and the final dark red product was collected by filtration (0.078 g, 40%). $^1$HNMR (DMSO-$d_6$):δ 8.20 (dd, 2H), 8.07 (dd, 2H), 7.83 (m, 2H), 7.71 (m, 2H), 3.13 (s, 3H) $^{13}$CNMR (DMSO-$d_6$): 183.32, 181.43, 179.53, 176.90, 153.42, 145.95, 141.32, 134.67, 134.48, 132.89, 131.92, 131.88, 131.81, 131.27, 126.87, 126.43, 126.35, 125.55, 125.04, 110.77, 43.93; $R_f$=0.6 (10:1 EtOAc:MeOH); mp=>150° C. (dec.); MS (ES+): 392.0.

3-chloro-3'-((2-(dimethylamino)ethyl)(methyl)amino)-[2, 2'-binaphthalene]-1,1',4,4'-tetrone (Compound 124).

In a 15 mL round bottom flask, 3,3'-dichloro-[2,2'-binaphthalene]-1,1',4,4'-tetrone 6 (0.306 g, 0.806 mmol), N,N,N'-trimethylethylenediamine (0.1 mL, 0.769 mmol), and DIEA (0.8 mL) were stirred in dichloromethane (10 mL) for 96 hours. The reaction solution was absorbed onto silica gel, and all volatile solvents were removed in vacuo. Column chromatography was performed (3:1 EtOAc/hexanes→EtOAc). The major product was a solid that was triturated with hexane to result in a red final solid (0.160 g, 41%). $^1$H NMR (CDCl$_3$) δ 8.22 (dd, 1H, J=6.0, 3.2 Hz), 8.16 (dd, 1H, J=6.0, 3.2 Hz), 8.03 (dd, 1H, J=8.0, 1.6 Hz), 7.99 (dd, 1H, J=8.0, 1.6 Hz), 7.81 (m, 2H), 7.67 (m, 2H), 3.94-3.88 (m, 1H), 3.58 (m, 1H), 2.94 (s, 3H), 2.85-2.77 (m, 2H), 2.31 (s, 6H); $^{13}$CNMR (CDCl$_3$): 182.07, 181.01, 177.82, 154.97, 146.31, 143.54, 134.64, 134.41, 133.97, 133.05, 132.78, 132.51, 132.41, 131.82, 127.81, 127.64, 126.36, 126.29, 114.11, 57.55, 52.87, 44.60, 42.71; $R_f$=0.33 (9:1 DCM/MeOH); mp=130° C. (dec.); MS (ES+): 449.0.

3-chloro-3'-[(2-hydroxyethyl)amino]-2,2'-binaphthalenyl-1,1',4,4'-tetrone (Compound 125).

In a 25 mL round bottom, 3,3'-dichloro-[2,2'-binaphthalene]-1,1',4,4'-tetrone 6 (0.508 g, 1.33 mmol), ethanolamine (0.09 mL, 1.49 mmol), and DIEA (1.5 mL) were stirred in dichloromethane (11 mL) for 24 hours. TLC of the reaction solution revealed a higher-running yellow spot and a lower-running red spot. Volatile solvents from the reaction solution were removed in vacuo. Column chromatography resulted in an orange-yellow solid which was characterized as the mono-aminated product (0.101 g, 29%). $^1$HNMR (DMSO-$d_6$): δ 8.15 (dd, 1H, J=6.8, 2.4 Hz), 8.06 (m, 2H), 7.93 (m, 3H), 7.68 (td, 1H, J=8.0, 1.2 Hz), 7.79 (td, 1H, J=8.0, 1.2 Hz), 7.34 (bs, 1H, NH), 4.78 (bs, 1H), 3.45 (m, 2H), 3.21 (m, 1H), 3.02 (m, 1H); $^{13}$CNMR (DMSO-$d_6$): 181.20, 181.05, 179.02, 177.06, 146.14, 143.84, 143.63, 135.44, 134.75, 134.56, 133.78, 132.90, 132.51, 131.51, 131.34, 129.88, 126.93, 126.90, 126.43, 125.67, 58.99, 46.16; $R_f$=0.34 (9:1 DCM/MeOH); mp=>180° C. (dec.); MS (ES+): 407.9.

3-chloro-3'-[(4-hydroxyethyl)piperazinyl]-2,2'-binaphthalenyl-1,1',4,4'-tetrone (Compound 126).

In a 25 mL round bottomed flask, 3,3'-dichloro-[2,2'-binaphthalene]-1,1',4,4'-tetrone (0.300 g, 0.78 mmol), 2-piperazinyl ethanol (1.2 eq), and DIEA (0.5 mL) were stirred in 10 mL of dichloromethane for 48 hours. All volatile materials in the reaction solution were removed in vacuo. The crude solid was preabsorbed onto silica gel and chromatographed in 50% EtOAc/hexanes→EtOAc. The final orange/red product was isolated in 24% yield (85 mg). $^1$H NMR (CDCl$_3$); 8.23 (dd, 1H, J=6.0, 2.4 Hz), 8.17 (dd, 1H, J=6,0, 2.4 Hz), 8.09 (dd, 1H, J=6.0, 2.4 Hz), 8.04 (dd, 1H, J=6.0, 2.4 Hz), 7.82 (m, 2H), 7.71 (m, 21H), 3.60 (m, 6H), 3.46 (m, 2H), 2.75 (m, 2H), 2.39 (m, 2H). $^{13}$CNMR (CD$_3$OD): 183.80, 183.09, 182.92, 178.50, 154.42, 145.85, 145.26, 135.91, 135.79, 135.66, 134.65, 133.65, 133.52, 133.48, 133.06, 128.47, 128.41, 128.09, 127.07, 115.84, 60.93, 58.88, 54.52, 51.12; $R_f$=0.31 (10:1 EtOAc:MeOH); mp=>158° C. (dec); MS (ES+): 477.1.

3-chloro-3'-(4-hydroxypiperidinyl)-2,2'-binaphthalenyl-1,1',4,4'-tetrone (Compound 127).

In a 50 mL round bottom flask, 3,3'-dichloro-[2,2'-binaphthalene]-1,1',4,4'-tetrone (0.334 g, 0.87 mmol), 4-hydroxypiperidine (0.132 g, 1.31 mmol), and DIEA (0.4 mL) were stirred in 10 mL of dichloromethane. The crude reaction mixture was preabsorbed onto silica gel and chromatographed (75% EtOAc/hexanes→5% MeOH/EtOAc). The middle spot was characterized as the mono-aminated product (76 mg, 20%). $^1$H NMR (DM SO-d$_6$) δ 8.23 (dd, 1H, J=4.0 Hz), 8.18 (dd, 1H, J=4.0 Hz), 8.10 (dd, 1H, J=4.0 Hz), 8.05 (dd, 1 H, J=4.0 Hz), 7.84-7.78 (m, 2H), 7.74-7.66 (m, 2H), 3.94 (m, 1H), 3.75 (m, 1H), 3.38 (m, 1H), 3.26 (m, 1H), 3.08 (m, 1H), 2.1-1.9 (m, 3H), 1.79 (m, 1H), 1.66 (m, 1H); $^{13}$CNMR (CDCl$_3$): 184.53, 184.07, 183.20, 182.61, 151.34, 151.07, 134.49, 134.13, 134.06, 133.16, 133.14, 132.90, 132.69, 132.48, 132.39, 126.73, 126.68, 126.63, 126.53, 123.32, 48.79, 48.55, 44.33, 35.22, 35.15; $R_f$=0.53 (EtOAc); mp=>195° C. (dec): MS (ES+): 457.0.

3,3'-bis-(2-dimethylamino)-2,2'-biuaphthalenyl-1,1',4,4'-tetrone (Compound 120).

In a pressure tube, 3,3'-dichloro-[2,2'-binaphthalene]-1,1',4,4'-tetrone (0.218 g, 0.569 mmol), dimethylamine hydrochloride (0.329 g, 4.03 mmol), and DIEA (0.7 mL) were stirred in 10 mL of dichloromethane for 48 hours. All volatile materials in the reaction solution were removed in vacuo. The crude solid was preabsorbed onto silica gel and chromatographed in 75% EtOAc/hexanes 7→100% EtOAc. The purified product was triturated with hexanes and ether (1:1, 5 mL), and the final dark red product was collected by filtration (0.110 g, 48%). $^1$H NMR (CDCl$_3$) δ 8.07 (dd, 2H, J=7.2, 1.6 Hz), 8.03 (dd, 2H, J=7.2, 1.6 Hz), 7.65 (m, 4H), 2.99 (s, 12H); $^{13}$CNMR (CDCl$_3$): 184.60, 182.64, 151.36, 134.07, 133.28, 132.65, 132.39, 126.59, 126.58, 120.33, 43.95; $R_f$=0.56 (10:1 EtOAc:MeOH); mp=>163° C. (dec.); MS (ES+): 401.1.

3,3'-bis({[2-(dimethylamino)ethyl]amino})-[2,2'-binaphthalene]-1,1',4,4'-tetrone (Compound 103).

The 3,3'-dichloro-[2,2'-binaphthalene]-1,1',4,4' tetrone (0.285 g, 0.75 mmol) was dissolved in 15 mL of dichloromethane in a 50 mL round-bottom flask, followed by sequential addition of N,N,N-trimethyl-ethylene diamine (0.28 mL, 2.98 mmol). The flask was then put under nitrogen and stirred for 24 hours. The product was washed three times with dichloromethane and a wash of 3 mL of sodium bicarbonate and filtered after adding magnesium sulfate to the flask. The remaining solution was preabsorbed onto silica gel and chromatographed (EtOAc→4:1 EtOAc/Methanol). Lastly, the desired product was vacuum filtered resulting in an 80% yield (290 mg) as a maroon/red powder. $^1$H NMR (CDCl$_3$) δ 8.11 (dd, 2H, J=7.6, 1.2 Hz), 8.08 (dd, 2H, J=7.6, 1.2 Hz), 7.71 (td, 2H, J=7.6, 1.2 Hz), 7.63 (td, 2H, J=7.6, 1.2 Hz), 6.84 (bs, 2H), 3.6-3.2 (bs, 4H), 2.6-2.4 (bs, 4H), 2.22 (s, 12H); $^{13}$CNMR (CDCl$_3$): 182.50, 182.03, 146.81, 134.87, 133.88, 132.34, 130.95, 127.08, 126.55, 118.20, 57.98, 45.07, 40,26; $R_f$=0.25 (1:1 EtOAc/Methanol); mp=120° C. (dec.); MS (ES+): 487.0.

3,3'-[(2-hydroxyethyl)amino]-2,2'-binaphthalenyl-1,1',4, 4'-tetrone (Compound 102).

The red solid with lower-running spot from the reaction of Compound 125 above was characterized as the bis amine Compound 102 (0.085 g, 15%). $^1$HNMR (DMSO-d$_6$): δ 8.03 (dd, 2H, J=7.6, 1.2 Hz), 7.95 (dd, 2H, J=7.6, 1.2 Hz), 7.85 (td, 2H, J=7.6, 1.2 Hz), 7.77 (td, 2H, J=7.6, 1.2 Hz), 6.86 (bs, 2H), 4.82 (t, 2H, J=4.8 Hz), 3.40 (m, 6H), 3.20 (m, 2H); $^{13}$CNMR (CDCl$_3$): 181.97, 180.11, 146.50, 134.84, 132.96, 132.31, 130.24, 126.62, 125.92, 125.78, 59.66, 44.98; $R_f$=0.30 (9:1 DCM/Methanol); mp=176° C. (dec); MS (ES+) 433.0.

3,3'-bis[4-(2-hydroxyethyl)piperazin-1-yl]-4a,5a-dihydro-[2,2'-binaphthalene]-1,1',4,4'-tetrone (Compound 121).

The 3,3'-dichloro-[2,2'-binaphthalene]-1,1',4,4' tetrone 6 (0.394 g, 1.03 mmol) was dissolved in 10 mL of dichloromethane in a 35 mL round-bottom flask, followed by sequential addition of 1-(2-hydroxyethyl)piperazine (0.543 g, 4.18 mmol). The flask was then put under nitrogen and stirred overnight. After 18 hours, the product was washed three times with dichloromethane and a wash of 3 mL of sodium bicarbonate and filtered after adding magnesium sulfate to the flask. The remaining solution was preabsorbed onto silica gel and chromatographed (DCM→20% MeOH/DCM). Lastly, the desired product was dissolved in diethyl ether and stirred for 10 minutes until it was vacuum filtered resulting in a 15% yield (84 mg) as a maroon/red powder, $^1$H NMR (CDCl$_3$) δ 808 (dd, 2H, J=5.6, 2.0 Hz), 8.06 (dd, 2H, J=1.2, 2.0 Hz), 7.69 (m, 4H), 3.59 (t, 4H), 3.52-3.44 (bs, 4H), 3.14-3.06 (m, 4H). 2.68-2.50 (m, 12H), 2.30-1.84 (bs, 2H); $^{13}$CNMR (CDCl$_3$): 183.77, 183.33, 150.60, 134.26, 133.15, 132.84, 132.45, 126.88, 126.75, 122.25, 59.66, 57.93, 53.61, 51.68; $R_f$=0.20 (9:1 DCM/Methanol); mp=171-174° C.; MS (ES+): 571.0.

3,3'-bis-(4-hydroxypiperidinyl)-2,2'-binaphthalenyl-1,1', 4,4'-tetrone (Compound 122).

The bottom spot from the reaction of Compound 127 above was characterized as the bis-aminated product (160 mg, 37%). $^1$H NMR (DMSO-d$_6$) δ 8.03 (dd, 2H, J=6.8, 1.2 Hz), 7.96 (dd, 2H, J=6.8, 1.2 Hz), 7.80 (m, 4H), 4.62 (d, 2H, OH, J=3.6 Hz), 3.60 (m, 4H), 3.08 (m, 4H), 2.68 (m, 1H), 1.82 (m, 4H), 1.55 (m, 2H), 1.45 (m, 2H), 1.22 (m, 1H); $^{13}$CNMR (DMSO-d$_6$): 183.07, 181.80, 150.27, 134.16, 132.99, 132.14, 131.84, 126.39, 125.53, 121.13, 64.91, 48.79, 34.97, 34.71; $R_f$=0.15 (EtOAC); mp=>137° C. (dec.); MS (ES+): 513.2.

3,3'-bis-[(2-hydroxyethyl)(N-methyl)amino]-2,2'-binaphthalenyl-1,1',4,4'-tetrone (Compound 107).

In a pressure tube, 3,3'-dichloro-[2,2'-binaphthalene]-1,1', 4,4'-tetrone (0.333 g, 0.869 mmol), 2-(methylamino)ethanol (0.07 mL, 0.875 mmol), and DIEA (1.1 mL) were stirred in dichloromethane (10 mL) for 48 hours. The reaction solution was absorbed with silica gel, column chromatography using 75:25 ethyl acetate:hexane solvent and ethyl acetate solvent.

The isolated dark solid was triturated with ether and hexane. to result in a dark red solid (165 mg, 45%). ¹HNMR (CDCl₃): δ 8.00 (m, 2H), 7.78 (in, 2H), 7.68 (m, 2H), 7.45 (m, 2H), 4.80 (m, 1H), 4.53 (m, 1H) 4.08 (m, 1H), 3.62 (m, 1H), 3.25 (m, 1H), 3.12 (s, 3H), 3.09 (s, 3H). ¹³CNMR (CDCl₃): 181.73, 180.41, 153.43, 133.69, 132.50, 132.29, 130.66, 128.23, 125.85, 124.10, 59.30, 49.54, 41.70; $R_f$=0.37 (10:1 EtOAc:MeOH); mp=118-122° C.; MS (ES+): 461.1.

3,3'-bis-[(2-methoxyethyl)(N-methyl)amino]-2,2'-binaphthalenyl-1,1',4,4'-tetrone (Compound 108).

In a pressure tube, 3,3'-dichloro-[2,2'-binaphthalene]-1,1',4,4'-tetrone 6 (0.300 g, 0.78 mmol), 2-methoxyethyl N-methylamine (3 eq), and DIEA (0.5 mL) were stirred in 10 mL of dichloromethane for 48 hours. All volatile materials in the reaction solution were removed in vacuo. The crude solid was preabsorbed onto silica gel and chromatographed in 40% EtOAc/hexanes→EtOAc. The purified product was triturated with hexanes and ether (1:1, 5 mL), and the final orange/red product was collected by filtration 139 mg (37%). ¹H NMR (400 MHz, CDCl₃): 8.06 (dd, 2H, J=6.4, 2.0 Hz), 8.00 (dd, 2H, J=6.4, 2.0 Hz), 7.66 (m, 4H), 3.71 (m, 6H), 3.43 (m, 2H), 3.30 (s, 6H), 2.99 (s, 6H); ¹³CNMR (CDCl₃): 184.04, 181.26, 152.69, 133.87, 132.66, 132.20, 132.18, 125.95, 125.26, 118.81, 70.31, 57.93, 53.99, 41.03; $R_f$=0.54 (10:1 EtOAc:MeOH); mp=139-142° C.; MS (ES+): 489.2.

3,3'-bis(4-(2-(2-hydroxyethoxy)ethyl)piperazin-1-yl)-[2,2'-binaphthalene]-1,1',4,4'-tetrone (Compound 110).

In a 25 mL round bottom, 3,3'-dichloro-[2,2'-binaphthalene]-1,1',4,4'-tetrone 6 (0.25 g, 0.654 mmol),1-[2-(2-hydroxyethoxy)ethyl]piperazine (0.16 mL, 0.975 mmol), and DIEA (0.50 mL) were stirred in dichloromethane (10 mL) for 24 hours under normal conditions. Excess DIEA was indicated in the crude spectra, so this material partitioned between 5 mL of water/DCM. The crude reaction mixture was pre-absorbed onto silica gel and chromatographed (80% DCM/MeOH). One pure fraction was concentrated and the desired product (28 mg, 7%) was characterized as described below. ¹H NMR (CDCl₃): δ 8.07 (d, 4H), 7.71 (t, 4H), 3.63 (m, 16H), 3.07 (t, 4H), 2.65 (m, 12H); ¹³CNMR (DMSO-d₆): 182.81, 181.80, 150.12, 134.16, 133.06, 131.93, 131.89, 126.39, 125.55, 72.46, 67.50, 60.12, 57.01, 53.33, 50.65; $R_f$=0.10 (1:10 MeOH:EtOAc); mp=>180° C. (dec.); MS (ES+): 659.2.

3,3'-bis({[2-(2-hydroxyethoxy)ethyl]amino})-2,3-dihydro-[2,2'-binaphthalene]-1,1',4,4'-tetrone (Si, Compound 111).

3,3'-Dichloro-[2,2'-binaphthalene]-1,1',4,4' tetrone (0.381 g, 1.0 mmol) was dissolved in 10 mL of dichloromethane in a 50 mL round-bottom flask, followed by sequential addition of 2-(2-aminoethoxy)ethanol (0.10 mL, 1.0 mmol) and DIEA (0.35 mL, 1.99 mmol). The flask was then put under nitrogen and stirred for 48 hours. The product was washed three times with dichloromethane and once with 3 mL of sodium bicarbonate. After adding magnesium sulfate to the flask, the contents were filtered. The remaining solution was preabsorbed onto silica gel and chromatographed (EtOAc→19:1 EtOAc/MeOH). Lastly, the desired product was dissolved in diethyl ether and stirred for 10 minutes until it was vacuum filtered, resulting in a 15% yield (84 mg) as a maroon/red powder. ¹H NMR (CDCl₃) δ 8.12 (dd, 2H, J=.8.4, 0.8 Hz), 8.10 (dd, 2H, J=8.4, 1.2 Hz), 7.73 (td, 2H, J=7.6, 1.6 Hz), 7.65 (td, 2H, J=7.6, 1.6 Hz), 6.41 (s, 2H), 3.80-3.40 (m, 16H), 2.70-2.40 (bs, 2H); ¹³C NMR (CDCl₃): 182.37, 182.02, 146.59, 135.08, 133.68, 132.52, 130.74, 127.12, 126.67, 110.29, 72.78, 69.74, 61.97, 43.31; $R_f$=0.32 (9:1 EtOAc/Methanol); mp=>120° C. (dee.); MS (ES+): 521.0.

3,3'-bis-(2-hydroxypropyl)-2,2'-binaphthalenyl-1,1',4,4'-tetrone (Compound 112).

In a 25 mL round bottom, 3,3'-dichloro-[2,2'-binaphthalene]-1,1',4,4'-tetrone (0.30 g, 0.783 mmol), racemic 1-amino-2-propanol (0.24 mL, 3.14 mmol), and DIEA (0.56 mL) were stirred in dichloromethane (10 mL) for 24 hours. The crude reaction mixture was preabsorbed onto silica gel and chromatographed using 98% DCM/methanol. One fraction was concentrated and the desired product (10 mg, 2.8%) was characterized as described below (mixture of diastereomers). (DMSO-d₆): δ 8.02 (d, 2H, J=7.6 Hz), 7.91 (d, 2H, J=7.6 Hz), 7.82 (td, 2H, J=7.6, 1.6 Hz), 7.75 (td, 2H, J=7.6, 1.6 Hz), 6.90 (bs, 1H, NH), 4.90 (m, 1H, OH), 3.60 (m, 1H), 3.35-2.90 (m, 2H), 0.85 (d, 0.5H, J=5.6 Hz), 0.80 (d, 2.5H, J=6.4 Hz); ¹³CNMR (CDCl₃): 183.64, 183.61, 183.58, 183.56, 182.10, 182.03, 181.98, 181.96, 148.20, 148.00, 136.09, 136.07, 135.10, 135.06, 135.03, 134.91, 134.90, 133.54, 132.07, 132.06, 128.20, 128.11, 127.81, 127.75, 127.57, 127.52, 127.35, 67.16, 67.05, 51.26, 51.24, 21.85, 21.64; $R_f$=0.49 (10:1 EtOAc:MeOH); mp=>147° C. (dec.); MS (E+) [M⁺Hr m/z: 461.0.

3,3'-bis-[(1-hydroxypropan-2-yl)amino-]-[2,2'-binaphthalene]-1,1',4,4'-tetrone (Compound 113).

The dichloride (0.305 g, 0.80 mmol), DCM (10 mL) and DIEA (0.206 g, 1.597 mmol) were added to a 50 mL round bottom flask, followed by the addition of (S)-(+)-2-amino-1-propanol (0.059 g, 0.80 mmol). The 50 mL round bottom flask was put under nitrogen and placed on a stir plate and allowed to stir over 48 hours. The crude mixture was washed with 0.1 N HCl (2-3 mL) to remove the excess base and starting material and separated. The organic layer was dried with MgSO₄ and concentrated. The crude solid was preabsorbed into silica gel and chromatographed (EtOAc). The dried product was a bright red solid (118 mg, 59%). ¹H NMR (CDCl₃): δ 8.11 (dd, 1H, J=5.6, 1.2 Hz), 8.09 (dd, 1H, J=5.6, 1.2 Hz), 7.72 (td, 1H, J=7.2, 1.6 Hz), 7.63 (td, 1H J=7.2, 1.6 Hz), 6.1 (bs, 1H, NH), 4.1 (m, 1H), 3.6 (dd, 1H, J=12.0, 3.6 Hz), 3.38 (dd, 1H, J=11.6, 8.8 Hz), 2.9 (s, 1H; OH), 0.9 (d, 2H, J=6.8 Hz); ¹³CNMR (CDCl₃): 182.37, 181.33, 135.25, 135.11, 133.95, 132.45, 130.81, 127.15, 127.06, 126.75, 67.29, 51.19. 18.31; mp=>205° C. (dec.); MS (ES+): 461.0.

2-hydroxy-7-methoxy naphthoquinone (Compound 142).

This compound was synthesized using a modification of the literature procedure: J. Org. Chem. 53:810-820, 1988. In dioxane (40 mL), 7-methoxy-1-tetralone (0.622 g, 3.53 mmol), KOH (1.116 g, 19.9 mmol), K₂CO₃ (2.573 g, 18.6 mmol), Re₂(CO)₁₀ (0.119 g, 0.182 mmol), and benzyltriethylammonium (catalyst) were stirred for 24 hours under oxygen bubbling. The reaction solution was acidified with concentrated HCl. The product was extracted from the reaction solution with ethyl acetate and dried with MgSO₄. Any volatile solvents were removed in vacuo. The crude product was triturated with 5 mL ether to result in a brown-orange solid (0.141 g, 19.6%). ¹HNMR (DMSO-d₆) δ 11.6 (s, 1H), 7.86 (s, 1H), 7.39 (d, 1H), 7.34 (d, 1H), 6.07 (s, 1H), 3.89 (s, 3H); ¹³CNMR (DMSO-d₆): 184.04, 181.19, 162.91, 159.14, 132.34, 127.80, 125.15, 120.02, 110.82, 109.93, 55.89; $R_f$=0.4 (EtOAc); MS (ES+): 205.0.

3,3'-Dichloro-6-methoxy-2,2'-binaphthalenyl-1,4,1',4'-tetrone (Compound 137).

This compound was synthesized by a modification of the literature procedure: J. Org. Chem. 69:5128, 2004. In acetonitrile (4 mL), Compound 142 (0.115 g, 0.563 mmol), 2,3-dichloro-1,4-naphthoquinone (0.179 g, 0.788 mmol), and cesium carbonate (0.325 g, 0.997 mmol) were stirred under nitrogen gas flow for 72 hours. The reaction solution was acidified with concentrated HCl and stirred. The resulting tan solid was filtered from the reaction solution and characterized as 3'-chloro-3-hydroxy-8-methoxy-2,2'-binaphthalenyl-1,4,1',4'-tetrone (Compound 135; 0.152 g, 68.4%). Under reflux, (0.138 g, 0.350 mmol), SOCl$_2$ (3 mL, 41 mmol), and DMF (5 drops) were stirred for 15 hours. The reaction solution was quenched with ice chips, and was extracted with dichloromethane and 5 mL of 10% NaHCO$_3$. All volatile solvents from the organic phase were removed in vacuo and the crude product was absorbed onto silica gel. Column chromatography was performed (20% hexanes/EtOAc→EtOAc) to afford a light yellow solid (0.090 g, 60%). This compound was characterized as the desired material.

3,3'-bis(2-hydroxyethylamino)-6-methoxy-2,2'-binaphthalenyl-1,1',4,4'-tetrone (Compound 104).

In a closed flask, Compound 137 (0.090 g, 0.210 mmol), ethanolamine (0.3 mL, 0.497 mmol), and DIEA (0.4 mL) were stirred in dichloromethane (3 mL) for 24 hours. The reaction solution was washed with 1 mL HCl 1M, 10% NaHCO$_3$ (1 mL), dried with MgSO$_4$ and absorbed onto silica gel. The crude product was purified with column chromatography (EtOAc→10% MeOH/EtOAc) to afford a red solid (0.020 g, 22.8%). $^1$HNMR (CD$_3$OD) δ 8.10 (d, 1H, J=7.2 Hz), 8.04 (d, 1H, J=7.2 Hz), 7.99 (d, 1H J=8.4 Hz), 7.80 (t, 1H, J=8.4 Hz), 7.78 (t, 1H, J=8.4 Hz), 7.58 (s, 1H), 7.28 (d, 1H, J=7.2 Hz), 3.95 (s, 3H), 3.60-3.36 (m, 8H); $^{13}$CNMR (CDCl$_3$): 174.00, 173.97, 173.39, 173.31, 155.11, 139.10, 126.34 (2C), 125.36, 124.22, 124.03, 122.55, 120.28 (2C), 118.44, 117.92 (3C), 112.03, 101.87, 52.08, 46.91, 38.67, 36.82; R$_f$=0.47 (10:1 EtOAc:MeOH); mp=>141° C. (dec.); MS (ES+): 463.0.

7-fluoro-2-hydroxy-1,4-naphthoquinone (Compound 143).

In dioxane (40 mL), 7-fluoro-1-tetralone (0.556 g, 3.37 mmol), KOH (0.992 g, 17.7 mmol), K$_2$CO$_3$ (2.315 g, 16.8 mmol), Re2(C0)10 (0.116 g, 1.78 mmol), and benzyltriethylammonium chloride (cat) were stirred for 72 hours under bubbling oxygen. The reaction solution was acidified with concentrated HCl. The product was extracted from the reaction solution with ethyl acetate and dried with MgSO$_4$. Any volatile solvents were removed in vacuo. The crude product was triturated with 5 mL ether and 2 mL hexane to result in a brown-orange solid (0.092 g, 14.2%). $^1$HNMR (Acetone-d$_6$) δ 11.8 (bs, 1H), 8.11 (dd, 1H, J=8.80, 5.2 Hz), 7.73 (dd, 1H, J=8.8, 2.4 Hz), 7.63 (td, 1H, J=8.8, 2.4 Hz), 6.25 (s, 1H); $^{13}$CNMR (Acetone-d$_6$): 184.95, 182.05, [168.12, 165.60, d, J$_{c-F}$=253.6 Hz], 134.52, 134.44, [130.79, 130.76, d, J$_{c-F}$=3.0 Hz], [130.61, 130.51, d, J$_{c-F}$=10.1 Hz], [122.90, 122.68, d, J$_{c-F}$=22.1 Hz], [113.90, 113.67, d, J$_{c-F}$=23.1 Hz], 112.31; R$_f$=0.31 (10:1 EtOAc:MeOH); mp=>190° C. (dec.); MS (ES+): 193.0.

3'-Chloro.-3-hydroxy-8-fluoro-2,2'-binaphthalenyl-1,4,1',4'-tetrone (Compound 136).

In acetonitrile (4 mL), 7-fluoro-2-hydroxy-1,4-napthoquinone (Compound 143; 0.082 g, 0.425 mmol), 2,3-dichloro-1,4-naphthoquinone, (0.112 g, 0.493 mmol), and cesium carbonate (0.350 g, 1.07 mmol) were stirred under nitrogen gas flow for 48 hours. The reaction solution was acidified with concentrated HCl and stirred. A brown solid was filtered from the reaction solution (0.110 g, 61.7%). $^1$HNMR (Acetone-d$_6$) δ 8.24 (m, 1H), 8.19 (dd, 1H, J=8.4, 4.8 Hz) 8.14 (m, 1H), 7.97 (m, 2H), 7.84 (dd, 1H, J=8.4, 2.8 Hz), 7.71 (td, 1H, J=8.4, 2.8 Hz); $^{13}$CNMR (CDCl$_3$): 181.92, 181.61, 181.13, 178.51, [168.44. 165.91, d, J$_{c-F}$=253.71], 146.61, 141.21, [136.24, 135.96, d, J$_{c-F}$=28.2 Hz], [134.34, 134.26 ,J$_{c-F}$=8.0 Hz], 133.24, 132.94, [131.28, 131.19, d, J$_{c-F}$=9.1 Hz], [130.48, 130.45, d, J$_{c-F}$=3.0 Hz], [128.58, 128.30, d, J$_{c-F}$=28.2 Hz], [123.52, 123.29, J$_{c-F}$=23.1 Hz], 117.43, [114.37, 114.13, J$_{c-F}$=24.2 Hz]; R$_f$=0.35 (10:1 EtOAc:MeOH); mp=>208° C. (dec.); MS (ES+): 381.2.

3,3'-dichloro-8-fluoro-2,2'-binaphthalenyl-1,4,1',4'-tetrone (Compound 138).

Under heating and nitrogen atmosphere, 3'-chloro-3-hydroxy-8-fluoro-2,2'-binaphthalenyl-1,4,1',4'-tetrone (0.095 g, 0.248 mmol), SOCl$_2$ (2.5 mL, 34 mmol), and DMF (5 drops) were stirred for 15 hours. The reaction solution was quenched with ice chips, and was extracted with dichloromethane and 5 mL NaHCO$_3$ 10% and dried with MgSO$_4$. All volatile solvents were removed in vacuo to afford a yellow solid (0.056 g, 56%). $^1$HNMR (DMSO-d$_6$) δ 8.16 (m, 2H), 8.08 (dd, J=6.0, 2.4 Hz), 7.98 (m, 2H), 7.92 (dd, 1H, J=8.8, 2.4 Hz), 7.81 (dt, 1H, J=8.8, 2.4 Hz) $^{13}$CNMR (CDCl$_3$): 189.31, 188.21, 185.91, 184.91, [d, 176.83, 174.11, J$_{c-F}$=272.1 Hz], 154.44, 150.40, 148.45, 144.85, [d, 143.71, 143.63, J$_{c-F}$=8.0 Hz], 140.71, 140.33, [d, 140.20, 140.10, J$_{c-F}$=8.0 Hz], 137.30, 137.02, 136.51, 131.95, 131.73, 130.55 [d, 123.77, 123.54, J$_{c-F}$=22.0 Hz]; R$_f$=0.63 (EtOAc); mp=>245 (dec.); MS (ES+): 400.7.

3,3'-bis(2-hydroxyethylamino)-6-fluoro-2,2'-binaphthyl-1,1',4,4'-tetrone (Compound 105).

Dichloride (50 mg, 0.12 mmol) was dissolved in DCM (2 mL) followed by addition of ethanolamine (30 μL, 4 equiv) and DIEA (100 μL xs). The reaction was stirred overnight and crude TLC indicated that the reaction was complete. The reaction was washed with water and the DCM layer was dried and chromatographed (DCM->10% MeOH/DCM), resulting in 15 mg of the desired product: $^1$HNMR (DMSO-d$_6$): δ 8.01-7.97 (m, 2H), 7.92 (d, 1H, J=7.6 Hz), 7.81 (t, 1H, J=7.6 Hz), 7.28 (m, 2H), 7.65 (dt, 1H, J=7.6, 2.4 Hz), 6.85 (bs, 2H), 4.79 (bs, 2H), 3.38 (m, 6H), 3.19 (m, 2H); $^{13}$CNMR (DMSO-d$_6$): 182.41, 181.62, 180.52, 179.64, 177.86, 177.60, 176.79, 176.38, 136.11, 135.99, 135.33, 135.03, 134.25, 133.91, 133.44, 133.19, 132.81, 130.74, 130.64, 130.53, 130.13, 129.65, 129.56, 127.11, 126.76, 126.41, 126.26, 124.52, 124.46, 122.24, 122.01, 121.94, 121.72, 113.31, 113.08, 112.85, 112.61, 60.47, 60.19, 49.51, 45.51; R$_f$=0.34 (EtOAc); mp=>144° C. (dec.); MS (ES+): 451.0.

3,3'bis-[(2-acyloxyethyl)amino]-2,2'-binaphthalenyl-1,-1',4,4'-tetrone (Compound 109).

In a 50 mL round bottom flask, a solution of MCD-66 (0.10 g, 0.23 mmol) in 7 mL dichloromethane was treated successively with DIEA (0.10 mL, 2.4 equiv.), acetic anhydride (0.05 mL, 2.2 equiv.), and 4-(dimethylamino)pyridine (10 mg, 0.08 mmol) and stirred overnight under nitrogen. The crude reaction mixture was preabsorbed onto silica gel and chromatographed (50% Hexane/EtOAc) to afford 11 mg (9%). $^1$HNMR (CD$_3$OD) δ 8.11 (dd, 2H, J=7.6, 1.2 Hz), 8.04 (dd, 2H, J=7.6, 1.2 Hz), 7.81 (td, 2H, J=7.6, 1.2 Hz), 7.78 (td, 2H, J=7.6, 1.2 Hz), 7.06 (bs, 2H), 4.05 (m, 4H), 3.62 (m, 4H), 1.85 (s, 6H); $^{13}$CNMR (CD$_3$OD): 187.22, 181.68, 178.73, 145.30, 140.93, 139.74, 138.5,0, 135.96, 133.79, 130.05, 127.58, 64.45, 58.68, 21.50; R$_f$=0.54 (EtOAc); mp=>146° C. (dec.); MS (ES+): 517.0.

Example 3. Chemical Synthesis of Compounds 101 and 106

2,3-dichloronaphthalene-1,4-dione (1; Compound 145) and 2-hydroxynaphthalene-1,4- dione (2; Compound 146)

were vigorously stirred together in the presence of Cs2CO3 for 7 days under an inert atmosphere, which, after acidification, furnished the biquinone (3; Compound 144). Oxalyl chloride effected the transformation of the hydroxyl group of (3) into a chlorine to deliver dichloro-biquinone (4; Compound 134). Finally, mono- and bis- aziridination of (4) was accomplished through treatment with limiting and excess amounts of aziridine to afford (5; Compound 106) and (6; Compound 101), respectively. See Scheme 5, below.

Scheme 5. Synthesis of Compounds 106 and 101.

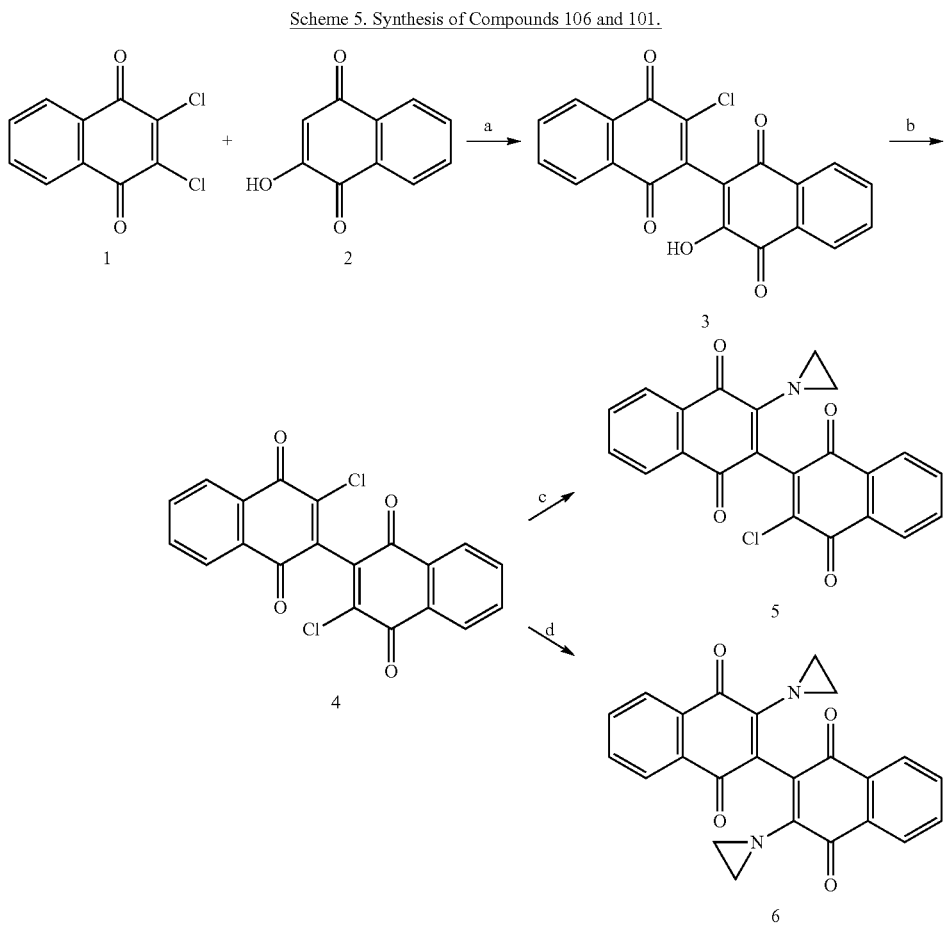

aziridinyl dimeric naphthoquinone Compound 101 exhibited activity against MOLM-14 cells and primary AML cells with IC50s of about 150-200 nanomolar and 2 micromolar, respectively.

The bis-aziridinyl dimeric naphthoquinone Compound 101 is more potent than the first generation dimeric naphthoquinone (chlorohydroxy dimeric naphthoquinone) or the mono-aziridinyl dimeric naphthoquinone as demonstrated by the IC50s generated in two AML cell lines, MOLM-14 and THP-1 (Table 5, below).

Example 4. Inhibition of Cell Proliferation IC50 Comparison with Compound 101

Figure 2A:
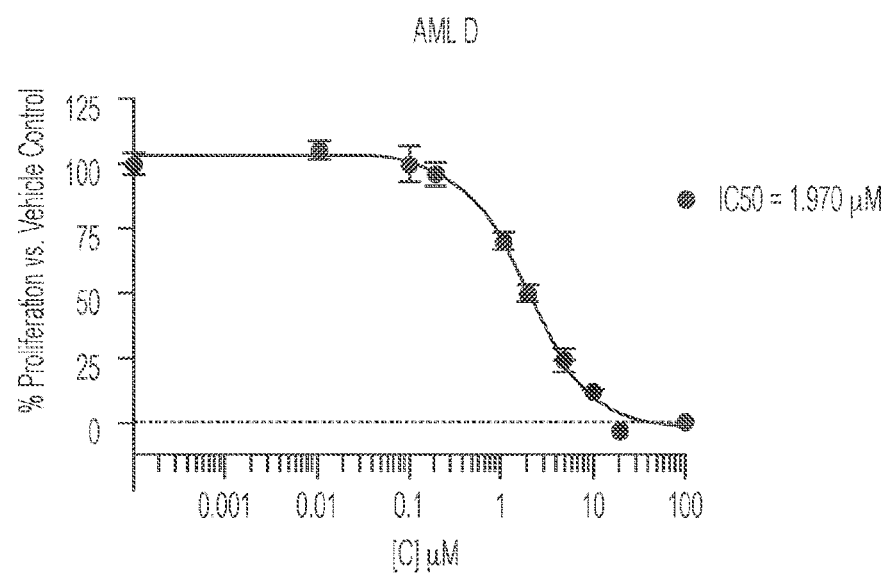
FIG. 2A, FIG. 2B and FIG. 2C are graphs showing the % proliferation versus control in AML-D (FIG. 2A), MOLM-13 (FIG. 2B), and normal bone marrow (FIG. 2C) cells.
Figure 2B:
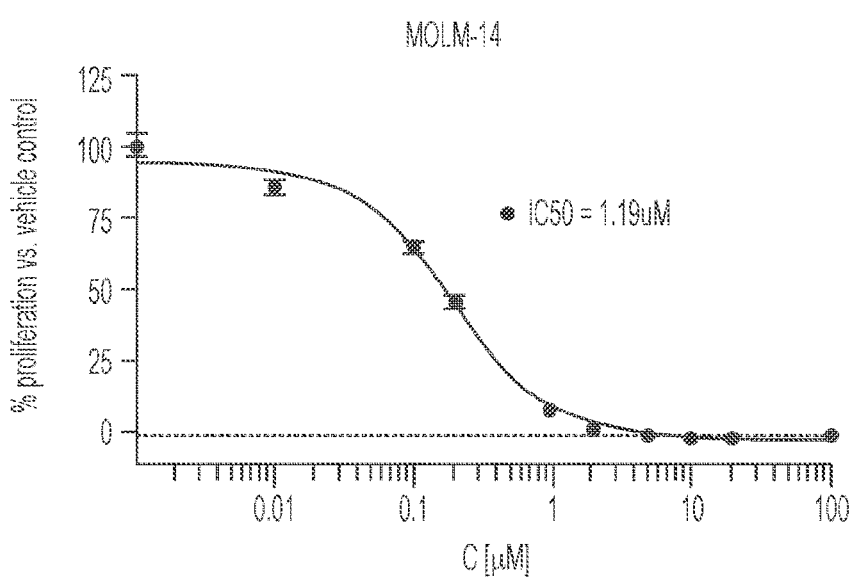
Figure 2C:
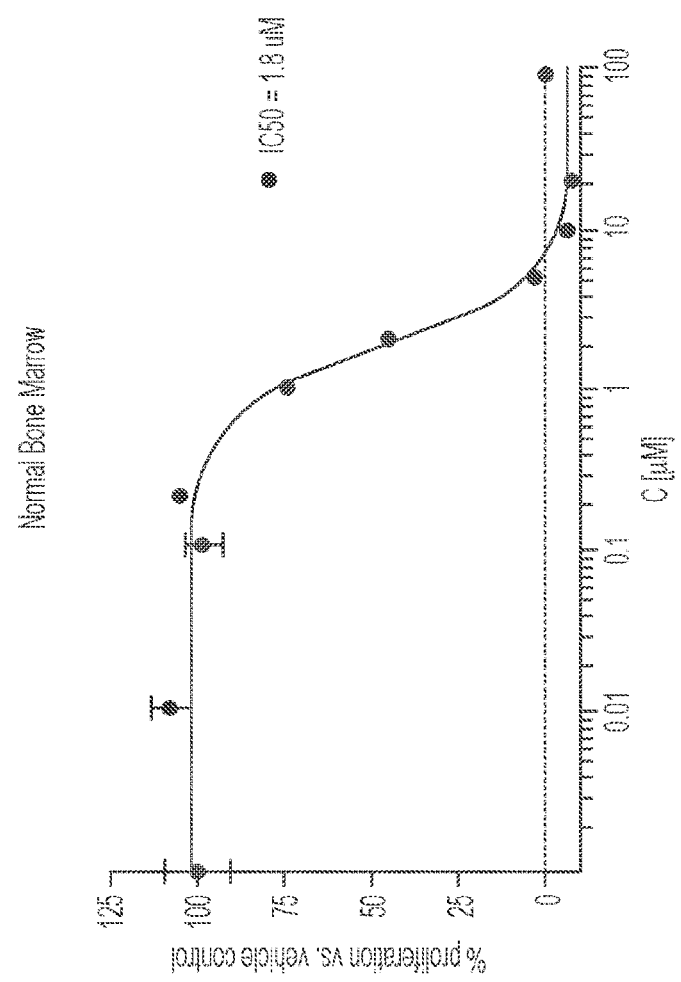

To investigate antiproliferative activity of amino-dimeric naphthoquinones against AML cells, an MTT-like cell proliferation assay was performed in the AML cell lines using WST-1 (water soluble tetrazolium salts; Promega®). MOLM-14 and AML-D cells, as well as normal hematopoietic bone marrow cells from a healthy donor, were exposed to a range of concentrations of Compound 101. Human leukemia cells were cultured in the presence of the compound for 72 hours (48 hours for primary cells) and WST-1 reagent was then added. The cells then were monitored for cell growth or the number of cells proliferating and the IC50 calculated. The IC50 is the concentration at which 50% of the cells are not proliferating compared to control cells treated with vehicle. See FIG. 2A, FIG. 2B, and FIG. 2C for representative graphs of these IC50 determinations. Bis-

TABLE 5

The IC50s of Dimeric Naphthoquinone Determined in Two AML Cell Lines.

| | MOLM-14 (n) | THP1 (n) |
|---|---|---|
| Chlorohydroxy dimeric naphthoquinone (representative data) | 3.3 µM | 10.9 µM |
| Mono-aziridine | 3.9 ± 1.0 µM | 7.7 ± 1.3 µM |
| Bis-aziridinyl | 0.25 ± 0.20 µM | 1.6 ± 1.0 µM |

Example 5. Antiproliferative Activity Against AML Cells

A concentration-dependent decrease in metabolic activity was observed in all cell lines after exposure to Compound 101, with IC50 values of 0.18±0.06 µM for MOLM-14, 1.05±0.05 µM for MV4-11, and 0.65±0.30 µM for THP-1 cells.

Compared to Compound 101, Compounds 106 and 114 demonstrated less potent anti-AML activities. IC50 values for Compound 106 were 3.9±1.0 µM for MOLM-14 and 7.7±1.3 µM for THP-1 cells. Compound 114 showed IC50s of 2.9±0.9 and 2.4±0.3 against MOLM-14 and MV4-11 cells, respectively.

Because Compound 101 demonstrated a superior potency, it was selected for testing against primary leukemia cells from patients and the remaining experiments including mechanistic assays. Table 6, below, summarizes the genetic characteristics of primary leukemia cells as well as their sensitivity to Compound 101. Mutations in the cells were as follows: A cells, FLT3-ITD with 84% allelic burden, NPM1-WT; B cells, FLT3-WT; C cells, DNMT3A mutated (c.2902G>A-p.R882), FLT3-WT, NPM1-WT, IDH1/IDH2-WT, CEBPα; D cells, FLT3-ITD (p.T582ins16) with 8% allelic burden, FLT3 point mutation (p.D835Y) with mutation level 29%, NMP1 mutation (p. Trp288Cysfs*12) with mutation level 454%, IDH1 (p.Arg132His) with mutation level 59%.

To measure the selectivity of Compound 101 against neoplastic cells, normal hematopoietic bone marrow cells were tested as well. Interestingly, the IC50 of bis-aziridinyl dimeric naphthoquinone Compound 101 for normal bone marrow cells was 3.37±1.27 µM, which was approximately five to eighteen times higher than those for AML cell lines and 1.5-2 times higher for primary leukemia cells, suggesting a favorable therapeutic index of this agent.

TABLE 6

Characteristics of Primary AML cells and Their Sensitivity to Compound 101.

| Cells | Leukemia Type | Karyotype | IC50 (µM) |
|---|---|---|---|
| A | Relapsed AML post-BMT | 46, XX, t(1; 5) (q25; q13)[5]/ 46, XX[15] | 2.84 |
| B | Chronic myelomonocytic leukemia (CMML) | 46, XY[20] | 2.08 |
| C | AML | 46-51, XY, +4, +8, +3mar[9] (trisomy 4, trisomy 8, and 3 marker chromosomes) | 2.25 ± 1.34 |
| D | AML | 46, XX[20] | 1.97 |

Example 6. Clonogenic Activity after Exposure to Compound 101

Figure 3A:
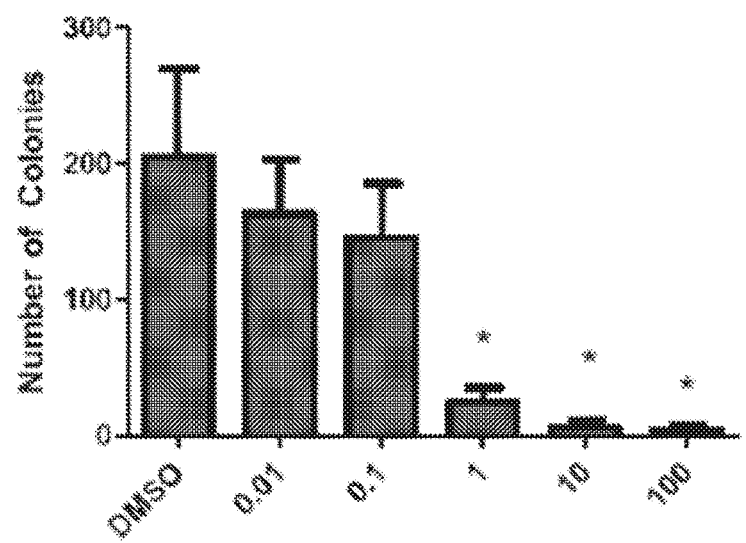
FIG. 3A and FIG. 3B show the number of clones in MOLM-14 and THP-1 cells, respectively, after treatment with Compound 101, also referred to as aziridinyl-BiQ, compared to DMSO.
Figure 3B:
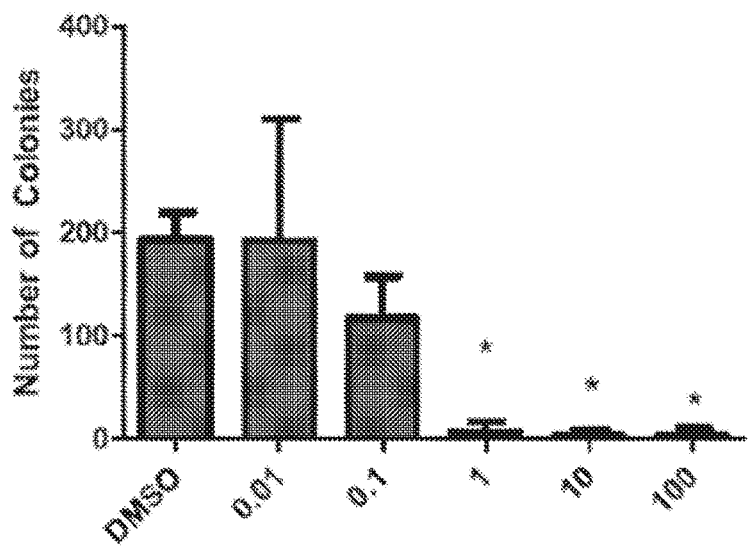

Next, the effect of bis-aziridinyl-dimeric naphthoquinone Compound 101 on AML cell survival and viability. Clonogenic activity is an in vitro assay to test the ability of every leukemic cell in a population to produce a colony by demonstrating neoplasticity and undergoing unlimited division. For colony formation assays, cell lines were treated with the indicated doses of aziridinyl dimeric naphthoquinone Compound 101 for 24 hours, and subsequently washed and plated in methylcellulose to observe clonogenic potential after 7-10 days. See above for additional comments on the methods. After 24 hours exposure to Compound 101, AML cell lines MOLM-14 and THP-1 exhibited marked reduction in clonogenic activity (FIG. 3A and FIG. 3B), which was statistically significant (p<0.05 for inhibition of colony formation at 1, 10, and 100 µM in both MOLM-14 and THP-1 cells.

Reduction of clonogenic activity was achieved at concentrations relative to the respective IC50 values of 3 for the AML cell lines (i.e. ≥1 µM). Moreover, this activity was observed with only 24 hours exposure and subsequent removal of Compound 101, and the trend held true for both MOLM-14 and THP-1 with different genetic characteristics. Similarly, cell survival decreased significantly in AML cells treated with Compound 101 for 72 hours, using trypan blue exclusion to detect dead cells on the automated cell counter.

Figure 3C:
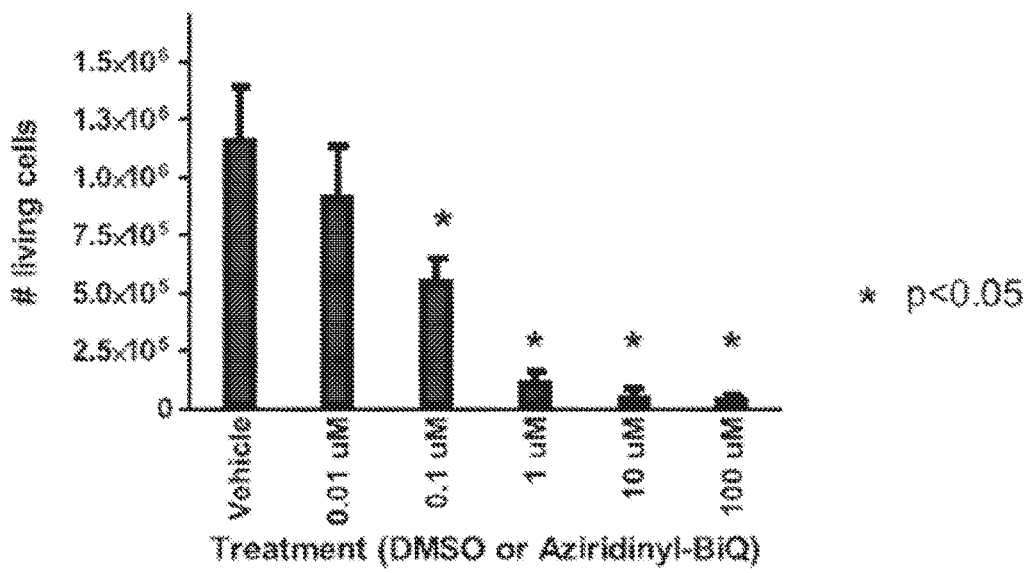
FIG. 3C and FIG. 3D show the numbers of living cells clones in MOLM-14 and THP-1 cells, respectively, after treatment with Compound 101, also referred to as aziridinyl-BiQ, compared to DMSO.
Figure 3D:
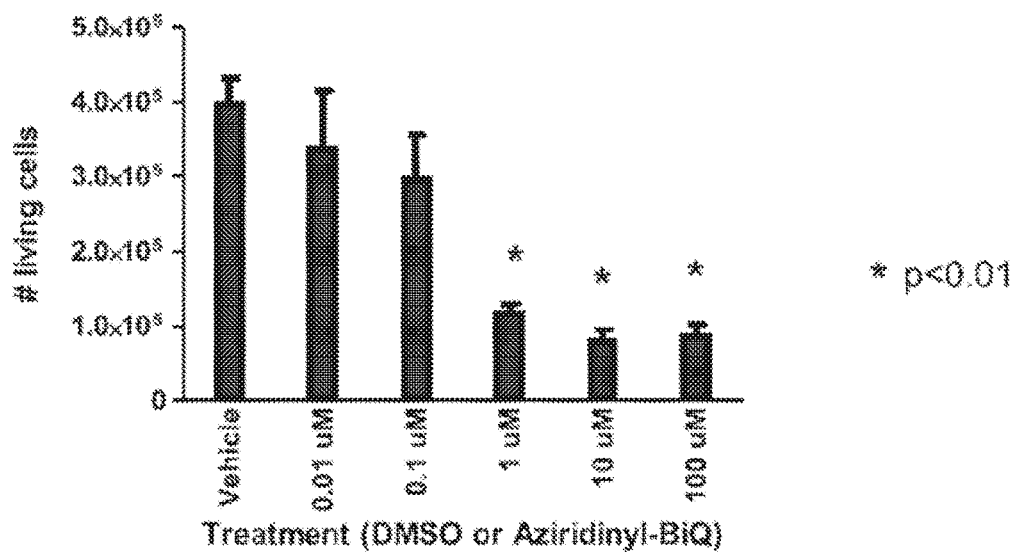

Cell survival was determined using trypan blue exclusion, in which cells are plated and the following day treated similarly to the proliferation assay. The bis-aziridinyl dimeric naphthoquinone Compound 101 was effective in decreasing cell number at increasing concentrations of compound in MOLM-14 and THP1 cells. After 72 hours, a statistically significant (p<0.05) reduction in viable cells was seen at 0.1, 1, 10, and 100 µM in MOLM-14, and at 1, 10, and 100 µM in THP-1 (see FIG. 3C and FIG. 3D). Thus, the bis-aziridinyl dimeric naphthoquinone (Compound 101) induced a dose-dependent reduction in cell survival, while a decrease in viable cells was observed with 1, 10 and 100 µM of first generation dimeric naphthoquinones.

Example 7. Clonogenic Activity

Figure 4A:
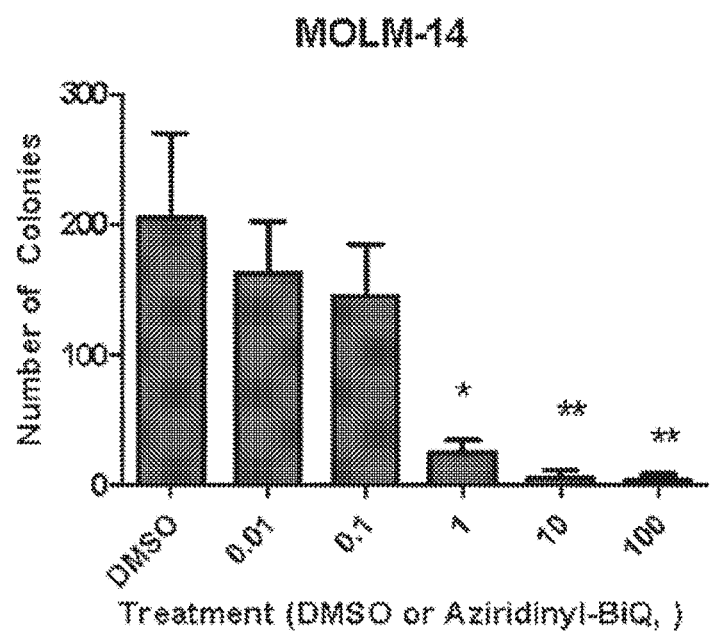
FIG. 4A and FIG. 4B are bar graphs showing the numbers of colonies of MOLM-14 (FIG. 4A) and THP-1 (FIG. 4B) cells, respectively.
Figure 4B:
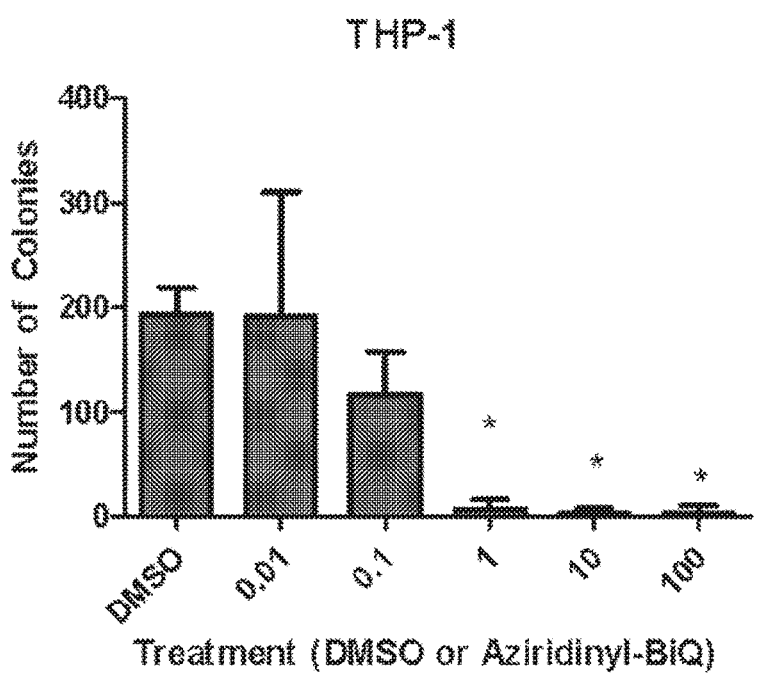

Bis-aziridinyl dimeric naphthoquinone (Compound 101 inhibits clonogenicity in MOLM-14 and THP-1 cells. See FIG. 4A and FIG. 4B. MOLM-14 and THP-1 were treated with Compound 101 for 24 hours and subsequently plated in methylcellulose with or without the compound present. Cells were allowed to grow for 7-12 days prior to termination and reading. The bis-aziridinyl dimeric naphthoquinone Compound 101 was effective in decreasing colony formation at increasing concentration of compound. At the end of treatment, at the higher concentrations of the bis-aziridinyl dimeric naphthoquinone, there were significantly fewer colonies than in the vehicle control (p<0.05) as denoted by the * in FIG. 4A. Clonogenic inhibition was not observed when bis-aziridinyl dimeric naphthoquinone was removed from cells after 24 hours of treatment. The bis-aziridinyl dimeric naphthoquinone was able to reduce clonogenicity with just a 24-hour exposure prior to plating. This means that Compound 101 is both more potent and a more effective anti-cancer agent than the first generation agents.

Example 8. Inhibition of Cell Proliferation

The IC50 for cell proliferation of compounds is contained in Table 7, Table 8, and Table 9, below. The methods used are described above in Example 1G and the compounds tested are indicated in the tables with the results.

TABLE 7

| | | | IC50 (μM) | |
|---|---|---|---|---|
| Compound | Structure | MW (amu) | MOLM-14 | MV411 |
| 102 | | 432.4 | 0.16 | 0.2 |
| 107 | | 460.5 | 6.3 | 5 |
| 108 | | 448.2 | 6.1 | 6 |
| 120 | | 400.4 | 2.9 | 2.4 |
| 123 | | 391.8 | 3 | 2.4 |

TABLE 7-continued

Structure-Activity Relationships.

| Compound | Structure | MW (amu) | IC50 (µM) MOLM-14 | MV411 |
|---|---|---|---|---|
| 124 | | 448.12 | 2.8 | 1.3 |
| 125 | | 407.8 | 2.2 | 1.2 |
| 126 | | 476.9 | 0.6 | 0.5 |
| 128 | | 446.1 | ND | ND |

TABLE 7-continued

Structure-Activity Relationships.

| Compound | Structure | MW (amu) | IC50 (μM) MOLM-14 | MV411 |
|---|---|---|---|---|
| 129 | | 507.9 | ND | ND |
| 134 | | 381.98 | ND | ND |
| 139 | | 443.6 | 7.1 | 5 |
| 144 | | 364.74 | 6.3 | 3 |

ND = not done

TABLE 8

Structure-Activity Relationships.

[Structure: 3-R-substituted naphthoquinone linked to 3-chloro-naphthoquinone]

| Compound | R | IC50 (μM) MOLM-14 | IC50 (μM) MV411 |
|---|---|---|---|
| 130 | –NH–CH$_2$CH$_2$–OH | 2.2 | 1.2 |
| 131 | –N(piperazine)–CH$_2$CH$_2$–OH | 0.85 ± 0.25 | 0.75 ± 0.35 |
| 132 | –N(4-hydroxypiperidin-1-yl) | 3.5 ± 0.63 | 2.1 ± 0.56 |

TABLE 8-continued

Structure-Activity Relationships.

[Structure: 3-R-substituted naphthoquinone linked to 3-chloro-naphthoquinone]

| Compound | R | IC50 (μM) MOLM-14 | IC50 (μM) MV411 |
|---|---|---|---|
| 142 | –N(CH$_3$)$_2$ | 2.99 ± 1.4 | 2.4 ± 2.0 |
| 143 | –NH–CH$_2$CH$_2$–N(CH$_3$)$_2$ | 2.8 ± 0.1 | 2.0 ± 1.0 |

TABLE 9

Structure-Activity Relationships.

| Compound | Structure | IC50 (μM) MOLM-14 | IC50 (μM) MV411 |
|---|---|---|---|
| 104 | [6-methoxy-naphthoquinone with two –NH–CH$_2$CH$_2$OH groups linked to a naphthoquinone] | 1.32 ± 0.23 | 2.05 ± 0.40 |
| 115 | [bis-naphthoquinone with two –NH–CH$_2$CH$_2$OH groups] | 0.15 ± 0.01 | 0.20 ± 0.02 |

TABLE 9-continued
Structure-Activity Relationships.
| Compound | Structure | IC50 (μM) MOLM-14 | MV411 |
|---|---|---|---|
| 116 | 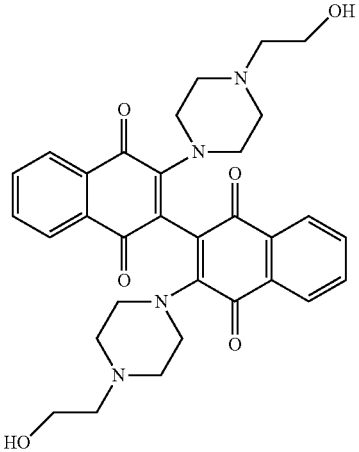 [SMILES: O=C1C(C2=C(N3CCN(CCO)CC3)C(=O)c3ccccc3C2=O)=C(N2CCN(CCO)CC2)C(=O)c2ccccc21] | 1.17 | 1.65 |
| 117 | 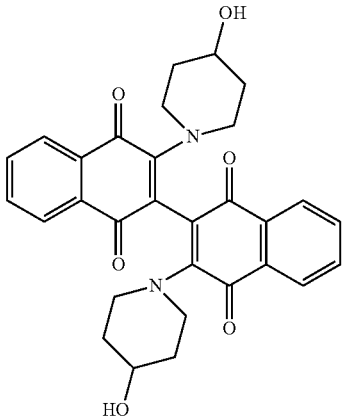 [SMILES: O=C1C(C2=C(N3CCC(O)CC3)C(=O)c3ccccc3C2=O)=C(N2CCC(O)CC2)C(=O)c2ccccc21] | 4.3 ± 2.1 | 2.5 |
| 118 | 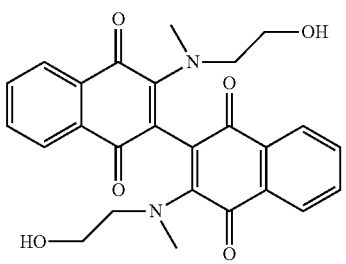 [SMILES: CN(CCO)C1=C(C2=C(N(C)CCO)C(=O)c3ccccc3C2=O)C(=O)c2ccccc2C1=O] | 5.8 ± 0.6 | 5.25 ± 0.3 |
| 119 | 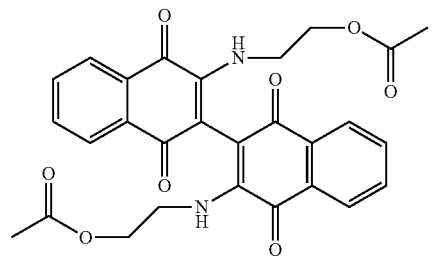 [SMILES: CC(=O)OCCNC1=C(C2=C(NCCOC(C)=O)C(=O)c3ccccc3C2=O)C(=O)c2ccccc2C1=O] | 1.0 | 2.2 ± 0.7 |

TABLE 9-continued

Structure-Activity Relationships.

| Compound | Structure | IC50 (μM) MOLM-14 | MV411 |
|---|---|---|---|
| 135 | | 2.8 ± 0.9 | 2.2 ± 0.6 |
| 136 | | ±1.42 | ±2.02 |
| 137 | | 0.37 ± 0.17 | 1.16 ± 0.2 |

Example 9. Compound 102 in Vitro Activity against AML Blasts

Two AML cell lines (MV4-11 & MOLM14) were treated with increasing doses of the clinically used naphthoquinones, atovaquone and vitamin K, as well as with Compound 102; and IC50 curves were generated with respect to cell proliferation as described above. See FIG. 5A. With nanomolar range IC50s, Compound 102 was 25-30 fold more potent than other naphthoquinones against AML cells. Compound 102 effectively inhibited clonogenicity of AML cells in a dose-dependent manner. When MV4-11 cells treated with Compound 102 at IC50 concentration, ROS levels significantly peaked after 2 hours and returned to baseline within 24 hours. The augmented production of ROS led to concomitant increase in DNA damage, evidenced by γH2AX foci in treated AML blasts.

Figures 5A, 5B:
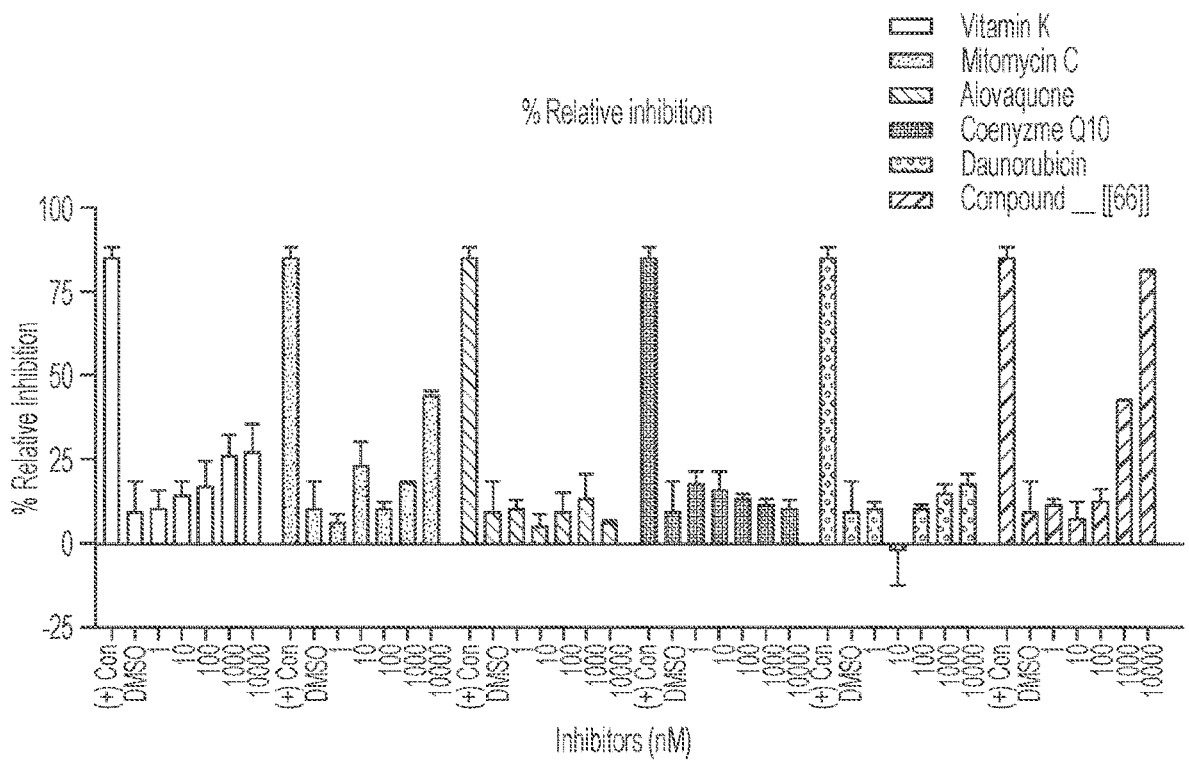
FIG. 5A is a table showing the IC50 of the indicated agents for cell proliferation in MV411 and MOLM-14 cells.
FIG. 5B is a bar graph showing the relative inhibition of the indicated agents in the indoleamine 2,3-dioxygenase 1 (IDO1) assay.

FIG. 5B shows results for IDO1 activity in the indicated compounds. Methods were as described and according to known methods. Compound 102 was found to inhibit IDO-1 activity at 1 μM (37%) and 10 μM (79%), but not its isozymes IDO-2 or tryptophan-2,3-dioxygenase (TDO). These results show that the amino-alcohol dimeric naphthoquinone Compound 102 has promising activity against AML blasts in vitro, with dual mechanisms of action. See FIG. 5B.

Example 10. Production of Reactive Oxygen Species

Figure 6A:
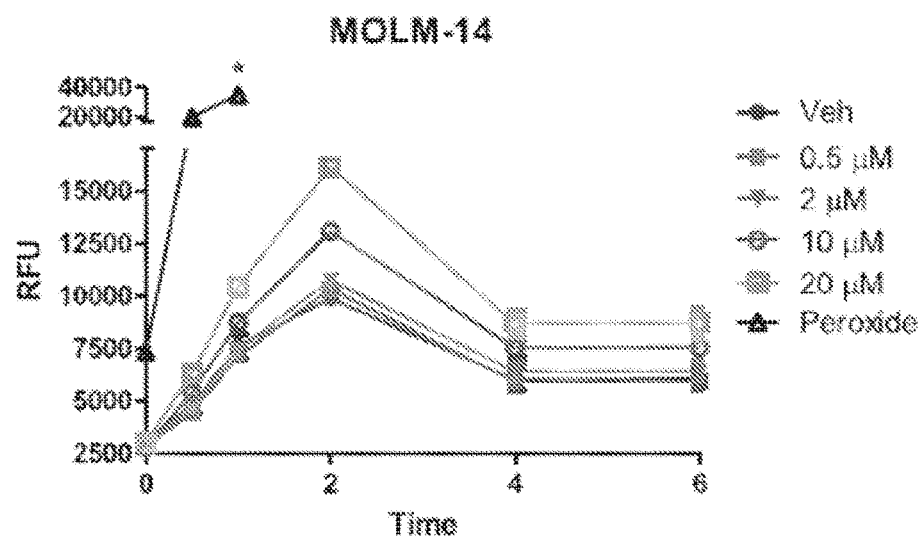
FIG. 6A and FIG. 6B are graphs showing the induced ROS production of the indicated cells (MOLM-14.
Figure 6B:
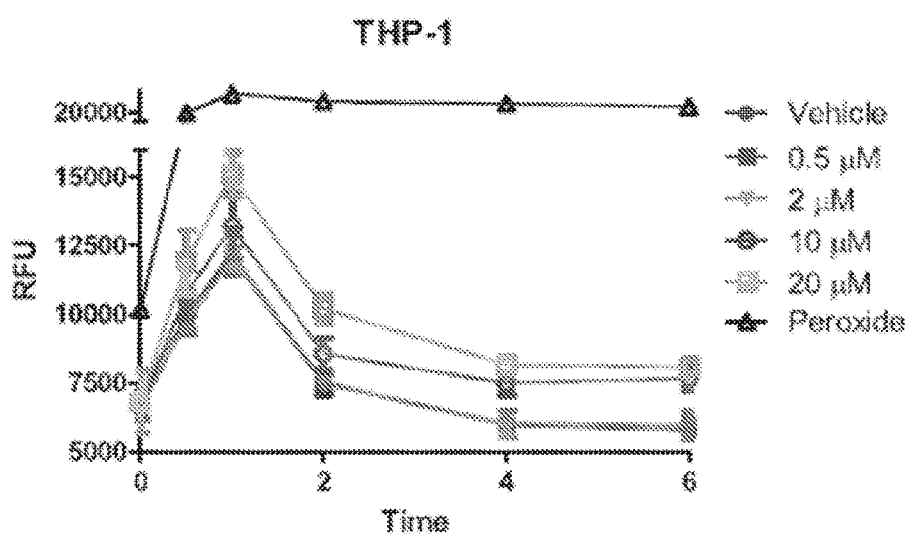

In order to elucidate the mechanisms by which the bis-aziridinyl naphthoquinone exerts anti-leukemic activity, the amount of reactive oxygen species (ROS) that cells produced upon treatment with Compound 101 was examined. MOLM-14 and THP-1 cells were loaded with the ROS dye $H_2DCFA$ and subsequently plated into 96-well plates. Cells were treated with vehicle (negative control), Compound 101 in varying concentrations, or hydrogen peroxide (positive control), and observed over a period of 2-6 hours. The relative fluorescence units (RFU) were read at various time points. Treatment with Compound 101 resulted in a rapid (within 2 hours) production of ROS. See results in FIG. 6A and FIG. 6B. A dose-dependent increase in ROS production was observed. *RFU went above the instrument detection limit. This effect also was dose-dependent and observable in both the MOLM-14 and THP-1 cell lines. Production of ROS is consistent with the ability of dimeric naphthoquinone moiety to undergo futile redox cycling.

Example 11. Double-Stranded DNA Break Induction

Taking into account the observed potent cytotoxicity towards AML cells and significant induction of ROS, whether Compound 101 (aziridinyl-BiQ 3) has any direct impact on DNA damage in AML cells was determined. To this end, the effect of treatment with Compound 101 on MOLM-14 cells was investigated to induce double-stranded DNA breaks.

Double-stranded DNA breaks are always followed by the phosphorylation of histone H2Ax (γ-H2Ax), a known biomarker for DNA damage. After only 24 hours exposure to physiologically relevant concentrations (200 nM, 1.0 and 2.0 µM) of Compound 101, MOLM-14 cells exhibited substantial γ-H2Ax phosphorylation, indicated by the present of the punctate pink foci (γ-H2Ax expression) observed in the nucleus of cells immunofluorescence). See FIG. 7. Similar to what was observed with ROS, colony formation and survival assays, this effect was strongly dose-dependent. See FIG. 7.

Figure 8:
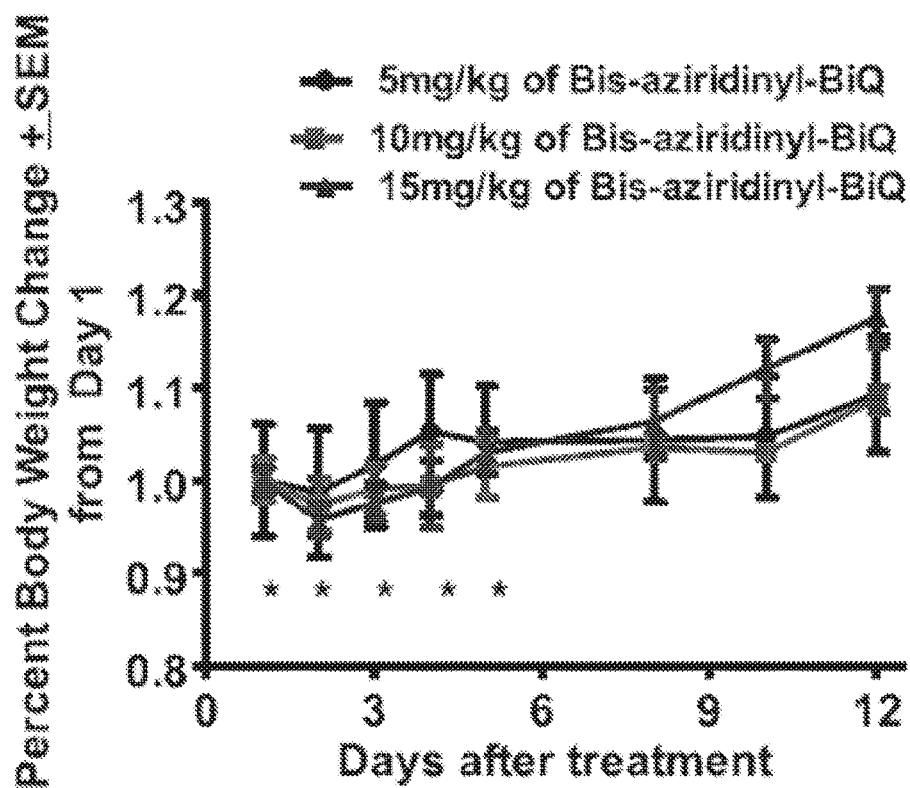
FIG. 8 is a graph showing the percent body weight change in mice treated with the indicated doses of Compound 102.

Example 12. Bis-Aziridinyl Dimeric Naphthoquinone (Compound 101) Effects in Vivo Considering the significant antineoplastic, activity of Compound 101, the safety and tolerability of this agent was tested in vivo on female NSG nice. Groups of three female NOD.Cg-Prkdc$^{scid}$ Il2rg$^{tm1Wjl}$/SzJ (NSG) mice were tested with 5, 10 or 15 mg/kg of Compound 101 delivered by intraperitoneal injection daily for 5 consecutive days, and the mice monitored for one additional week. As shown in FIG. 8, the mice tolerated the compound well with no weight loss observed during the 5 days of dosing and one week observation period. An asterisk (*) denotes days of dosing. Mean body weight loss did not exceed 10%.

Example 13. Activity of Compound 102

Figure 9A:
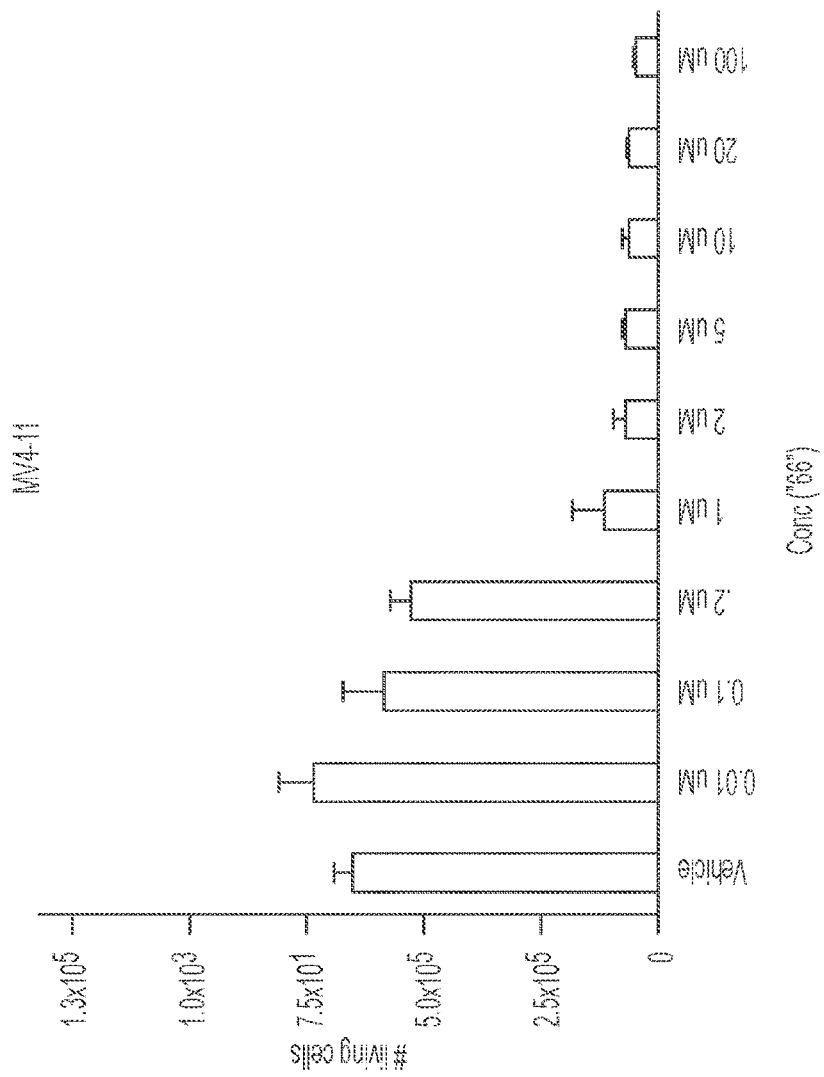
FIG. 9A shows the number of living cells in MV4-11 cells after treatment with the indicated concentrations of Compound 102.

Cell survival was determined using trypan blue exclusion as described above, in which cells are plated and the following day treated similarly to the proliferation assay. Compound 102 (also referred to here as "66") was effective in decreasing cell number at increasing concentrations of compound in MV4-11 cells. See FIG. 9A. Thus, Compound 102 induced a dose-dependent reduction in cell survival.

Figure 9B:
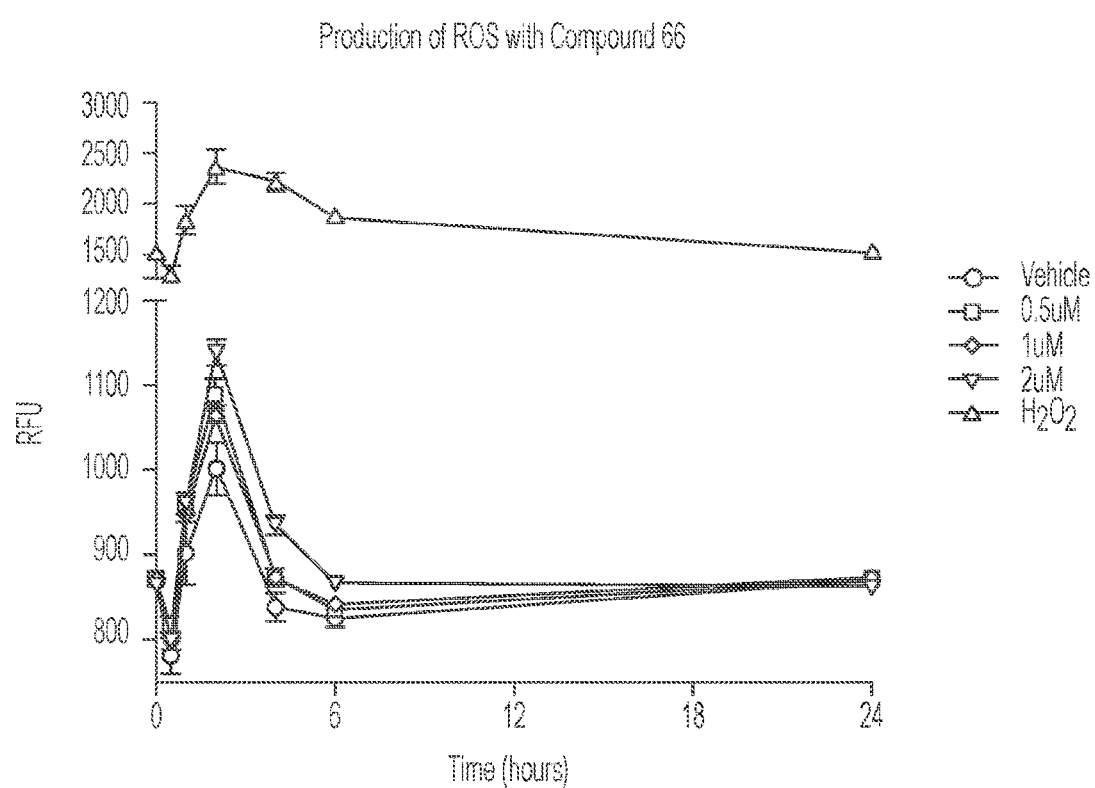
FIG. 9B shows production of ROS in cells after treatment with the indicated concentrations of Compound 102, also referred to here as "66."

The amount of reactive oxygen species (ROS) that cells produced upon treatment with Compound 102 then was examined. See results in FIG. 9B. The cells were loaded with the ROS dye H$_2$DCFA and subsequently plated into 96-well plates. Cells were treated with vehicle (negative control), Compound 102 in varying concentrations, or hydrogen peroxide (positive control), and observed over a period of 2-6 hours. The relative fluorescence units (RFU) were read at various time points. Treatment with Compound 102 resulted in a rapid production of ROS. See results in FIG. 9B. A dose-dependent increase in ROS production was observed. Production of ROS is consistent with the ability of Compound 102 to undergo futile redox cycling.

REFERENCES

All references cited herein are hereby incorporated by reference in their entirety.

Alibbai et al., Cancer 115:2903-2911, 2009.
Carter-Cooper et al., Bioorg. Med. Chem. Lett. 27:6-10, 2017.
Chakrabarti et al., Cancer Metab. 3:12, 2015.
Danson et al., Ann. Oncol.: J. Eur. Soc. Med. Oncol. 22:1653-1660, 2011.
Eberlein et al., PloS one 10:e0123174, 2015.
Emadi et al., Organic Lett. 4:521-524, 2002.
Emadi et al., Nat. Rev. Clin. Oncol. 6:638-617, 2009.
Emadi et al., PloS one 5:e10846, 2010.
Emadi et al., Bioorg. Med. Chem. 19:7057-7062, 2011,
Emadi and Karp, Pharmacogenomics 13:1257-1269, 2012.
Emadi and Karp, Leuk. Lymph. 55:2423-2425, 2014.
Frank et al., Invest. New Drugs 34(6):693-700, 2016.
Hole et al., Blood 117:5816-5826, 2011.
Lapidus et al., Pharmaceuticals 9(1):pii:e4, 2016.
Oran and Weisdorf, Haematologica 97:1916-1924, 2012.
Papaemmanuil et al., N.E.J.M. 374:2209-2221, 2016.
Patel et al., N.E.J.M. 266:1079-1089, 2012.
Pidugu et al., BMC Structural Biol. 16:1-10, 2016.
Ross et al., BJU Intl. 108:447-454, 2011.
Stagliano et al., Bioorg. Med. Chem. 14:5651-5665, 2006.
Turinetto et al., Mol. Carcinogenesis 55(11):1833-1842, 2015.
Verma, Anti-Cancer Agents Med. Chem. 6:489-499, 2006.
Wellington, Roy. Soc. Chem. Adv. 5:20309-20338, 2015.
Workman, Oncol. Res. 6:461-475, 1994.
Xiang et al., Blood 128(14):1845-1853, 2016.

The invention claimed is:

1. A compound according to Formula A,

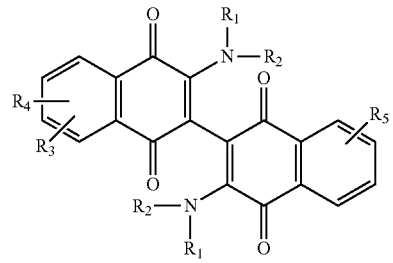

Formula A wherein $R_1$ and $R_2$, independently are the same or different and are selected from the group consisting of —Cl, —Br, —I, —F, —H, —CH$_3$, —CH$_2$CH$_3$, —CH$_2$OH, —CH$_2$CH$_2$OH, —CH(CH$_2$OH)$_2$, —CH=CHOH, —CH$_2$CH(CH$_3$)OH, —CH$_2$CH(CH$_3$)CH$_2$CH$_2$OH, —CH$_2$CH$_2$OCH$_2$OH, —CH$_2$CH$_2$OCH$_2$CH$_2$OH, —CH$_2$CH$_2$OCH$_3$, —CH$_2$CH$_2$OCOCH$_3$, —CH$_2$NH$_2$, —CH$_2$NHCH$_3$, —CH$_2$N(CH$_3$)$_2$, —CH$_2$CHN(CH$_3$)$_2$, and —CH$_2$X, or $R_1$ and $R_2$ can be joined to form a cyclic

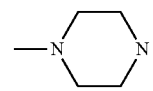

1-piperizino which optionally is substituted at the 4-position with hydroxyl, hydroxymethyl, —CH$_2$CH$_2$OCH$_2$OH, or —CH$_2$CH$_2$OCH$_2$CH$_2$OH,

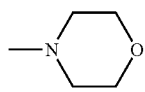

morpholino, or aziridino; and wherein $R_3$ and $R_4$, independently are the same or different and are selected from the group consisting of —H, —NH$_2$, —X, —CH$_3$ optionally substituted with one or more X, —OH, —OCH$_3$ optionally substituted with one or more X, —OCH$_2$CH$_3$ optionally substituted with one or more X, —OCH$_2$CH$_2$CH$_3$ optionally substituted with one or more X, —CH$_2$OCH$_3$ optionally substituted with one or more X, —C(O)CH$_3$, —C(O)H, —C(O)OH, —CH$_2$C(O)OH, —NO$_2$, —CH$_2$NO$_2$, —CN, and —CH$_2$CN, and —SO$_2$—R$_5$;

wherein X is halo and $R_5$ is H or $C_{1-3}$ alkyl;

or a salt, hydrate, or solvate thereof, with the proviso that when $R_1$ and $R_2$ are —H, —CH$_2$CH$_3$, or —CH$_3$, then $R_5$ is not —H or —CH$_3$.

2. The compound of claim 1, wherein $R_1$ and $R_2$ independently are the same or different and are selected from the group consisting of aziridino, hydroxyl, chloro, —CH$_2$CH$_2$OH and —CH$_2$CH$_2$N(CH$_3$)$_2$.

3. The compound of claim 1, wherein $R_3$ and $R_4$ independently are the same or different and are selected from the group consisting of —H, —F, —Cl, —CF$_3$, —OH, —OCH$_2$CH$_3$ and —OCH$_3$.

4. A compound selected from the group consisting of:

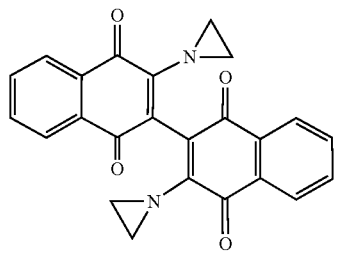

(3,3'-bis(aziridine)-2,2'-binaphthoquinone)

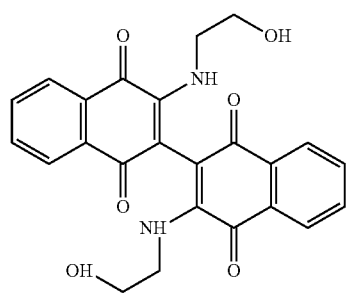

(3,3'-bis(2-aminoethanol)-2,2'-binaphthoquinone)

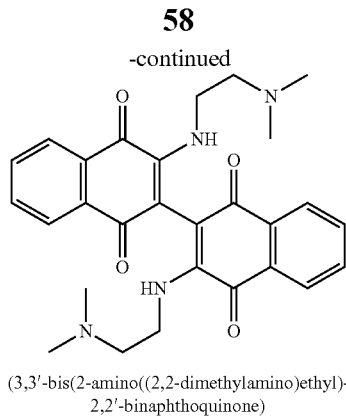

(3,3'-bis(2-amino((2,2-dimethylamino)ethyl)-2,2'-binaphthoquinone)

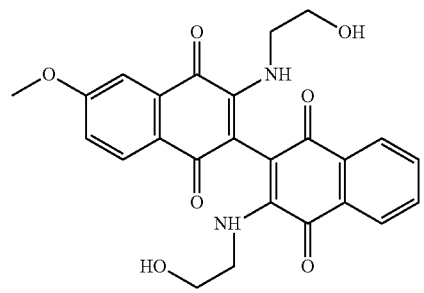

(6-methoxy, 3,3'-bis(2-aminoethanol)-2,2'-binaphthoquinone)

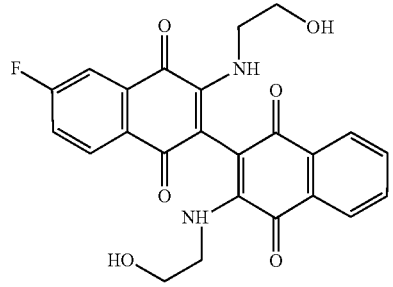

(6-fluoro,3,3'-bis(2-aminoethanol)-2,2'-binaphthoquinone) and

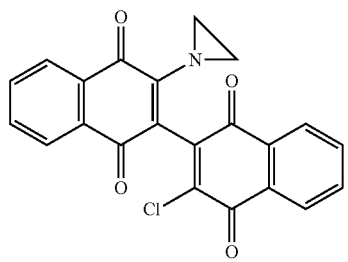

(3-(aziridin-1-yl)-3'-chloro-[2,2'-binaphthalene]-1,1'4,4'-tetrone)

5. The compound of claim 4, which is:

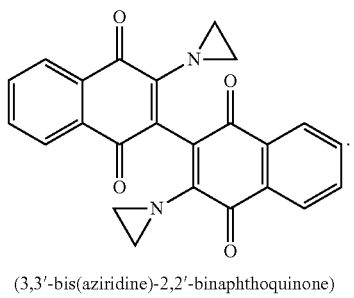 [SMILES: O=C1C(C2=C(N3CC3)C(=O)c3ccccc3C2=O)=C(N2CC2)C(=O)c2ccccc21]

(3,3'-bis(aziridine)-2,2'-binaphthoquinone)

6. The compound of claim 4, which is:

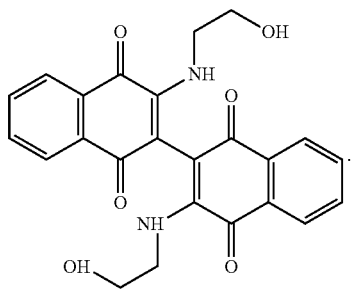

(3,3'-bis(2-aminoethanol)-2,2'-binaphthoquinone)

7. The compound of claim 4, which is:

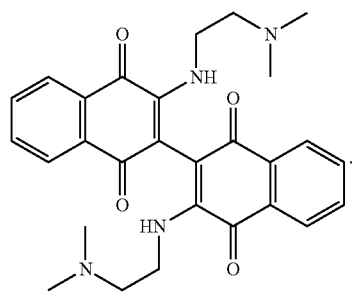

(3,3'-bis({[2-(dimethylamino)ethyl]amino})-2,2'-binaphthalene]-1,1',4,4'-tetrone)

8. The compound of claim 4, which is:

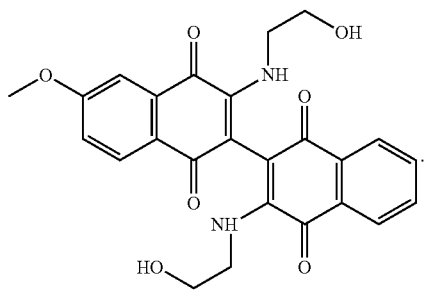

(6-methoxy, 3,3'-bis(2-aminoethanol)-2,2'-binaphthoquinone)

9. The compound of claim 4, which is:

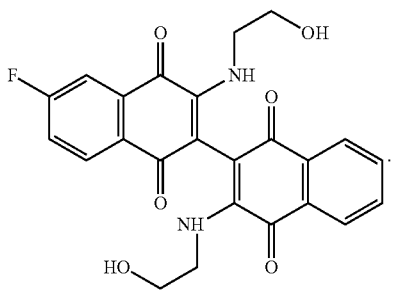

(6-fluoro, 3,3'-bis(2-aminoethanol)-2,2'-binaphthoquinone)

10. The compound of claim 4, which is:

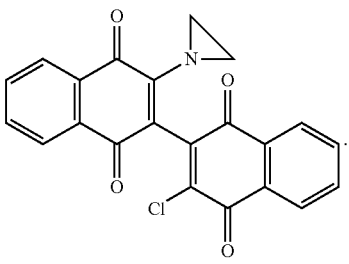

(3-(aziridin-1-yl)- 3'-chloro-[2,2'-binaphthalene]-1,1' 4,4'-tetrone)

11. A pharmaceutical composition comprising a compound of claim 1 and a pharmaceutically acceptable carrier.

12. A pharmaceutical composition comprising a compound of claim 4 and a pharmaceutically acceptable carrier.

13. A method of treating leukemia comprising administering to a subject in need a pharmaceutical composition of claim 11.

14. A method of treating leukemia comprising administering to a subject in need a pharmaceutical composition of claim 12.

15. A method of claim 13, further comprising administering to the subject in need a second pharmaceutical agent.

16. A method of claim 14, further comprising administering to the subject in need a second agent.

17. A method of claim 15, wherein the second agent is selected from the group consisting of Cytarabine, Daunorubicin, Daunomycin, Idarubicin, mitoxantrone, Cladribine, Fludarabine, Topotecan, Etoposide, 6-thioguanine, Hydroxyurea, Methotrexate, 6-mercaptopurine, Azacitidine, and Decitabine.

18. A method of claim 16, wherein the second agent is selected from the group consisting of Cytarabine, Daunorubicin, Daunomycin, Idarubicin, mitoxantrone, Cladribine, Fludarabine, Topotecan, Etoposide, 6-thioguanine, Hydroxyurea, Methotrexate, 6-mercaptopurine, Azacitidine, and Decitabine.

19. The method of claim 13, wherein the leukemia is acute myeloid leukemia.

20. The method of claim 14, wherein the leukemia is acute myeloid leukemia.

21. A method of treating acute myeloid leukemia comprising administering to a subject in need a pharmaceutical composition of claim 11.

22. A method of treating acute myeloid leukemia comprising administering to a subject in need a pharmaceutical composition of claim 12.

* * * * *